United States Patent [19]
Parker et al.

[11] Patent Number: 5,985,616
[45] Date of Patent: Nov. 16, 1999

[54] CHIMERIC MAMMALIAN NPY $Y_5$ RECEPTORS

[75] Inventors: Eric McFee Parker, Scotch Plains; Catherine Devine Strader, Verona; Mark Stephen Rudinski, Morristown, all of N.J.

[73] Assignee: Schering Corporation, Kenilworth, N.J.

[21] Appl. No.: 09/003,199

[22] Filed: Jan. 7, 1998

[51] Int. Cl.[6] ..................................................... C12N 15/62
[52] U.S. Cl. ................ 435/69.7; 435/252.3; 435/254.11; 435/320.1; 435/325; 536/23.4; 536/23.5
[58] Field of Search .................. 536/23.5, 23.4; 435/69.7, 325, 320.1, 252.3, 254.11

[56] References Cited

U.S. PATENT DOCUMENTS 5,602,024  2/1997  Gerald ...................................... 435/325

FOREIGN PATENT DOCUMENTS

WO 97/17440   5/1997   WIPO .

OTHER PUBLICATIONS

Wilding, J., et al., (1993), Increased Neuropeptide–Y Messenger Ribonucleic Acid (mRNA) and Decreased Neurotensin mRNA in the Hypothalamus of the Obese (ob/ob) Mouse, *Endocrinology*, vol. 132, pp. 1939–1944.

Woldbye, D., et al., (1997) Powerful inhibition of kainic acid seizures by neuropeptide Y via Y5–like receptors, *Nature Medicine*, vol. 3, pp. 761–764.

Gerald, C., et al., (1996), A receptor subtype involved in neuropeptide–Y–induced food intake, *Nature*, vol. 382, pp. 168–171.

Howlett, R., (1996), Prime Time for neuropeptide Y, *Nature*, vol. 382, p. 113.

Hu, Y., et al., (1966), Identificaiton of a Novel Hypothalamic Neuropeptide Y Receptor Associated with Feeding Behavior, *The Journal of Biological Chemistry*, vol. 271, pp. 26315–26319.

Sperk, G., et al., (1997), Anticonvulsant action of neuropeptide Y, *Nature Medicine*, vol. 3, pp. 728–729.

Stephens, T., et al., (1995), The role of neuropeptide Y in the antiobesity action of the obese gene product, *Nature*, vol. 377, pp. 530–532.

Wahlestedt, C., et al., (1993), Neuropeptide Y–Related Peptides and Their Receptors—Are the Receptors Potential Therapeutic Drug Targets?, *Annual Reviews Pharmacol. Toxicol.*, , vol. 32, pp. 309–352.

Akabayashi, A., et al., (1994), Hypothalamic neuropeptide Y, its gene expression and receptor activity: relation to circulating corticosterone in adrenalectomized rats, *Brain Research.*, vol., 665, pp. 202–212.

Bischoff, A., et al., (1997), Receptor subtypes $Y_1$ and $Y_5$ are involved in the renal effects of neuropeptide Y, *British Journal of Pharmacology*, vol. 120, pp. 1335–1343.

Blomqvist, A., et al., (1997), Y–receptor subtypes—how many more?, *Trends Neurosci.*, vol. 20, pp. 294–298.

Cheng, Y., et al., (1973), Relationship Between the Inhibition Constant ($K_1$) and the Concentration of Inhibitor Which Causes 50 Per Cent Inhibitor ($I_{50}$) of an Enzymatic Reaction, *Biochemical Pharmacology*, vol. 22, pp. 3099–3108.

Dube, M., et al., (1994), Evidence that neuropeptide Y is a physiological signal for normal food intake, *Brain Research*, vol. 646, 341–344.

Erickson, J., et al., (1996), Attenuation of the Obesity Syndrome of ob/ob Mice by the Loss of Neuropeptide Y, *Science*, vol. 274, pp. 1704–1707.

*Primary Examiner*—Sally P. Teng
*Attorney, Agent, or Firm*—Immac J. Thampoe

[57] ABSTRACT

The present invention provides mammalian chimeric NPY $Y_5$ receptors, nucleic acids and vectors encoding the receptors, methods for making the receptors, fragments or fusion proteins thereof using recombinant DNA methodology or chemical synthesis, and methods for using the receptors in screening systems to identify compounds for the treatment of various diseases.

5 Claims, No Drawings

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
       (A) LENGTH: 1672 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 300..1634

(xi) SEQUENCE DESCRIPTION: SEQ ID NO:1:

```
GGATCCCCGA GGTGCTTCTA AAACCCTGGC GGCTCCGGAG CCCCTCCTTC CCACCACCGC     60

CTCCAGGTCC TGCTCCTGCC GCCACCGCTT CCATCTGGAG CAGAAGCGAC CGCGCTCAGC    120

CACGTACCCC GGAGTCCAGG CACCCGCAGC GGCCGGGGCA TCCCGAGCTG CCATACACC     180

GGGAGACAGC TGTGCCCTTG GGTTTGCAAG GTGGCTTGGA AGTCAACTGC CAGTAGGAAA    240

TAGCCATCCA CACACCTGAG TTCCAAGGGG GAAGAAAGAG ATTCTTATCT GATTCTAGT     299

ATG GAG TTT AAG CTT GAG GAG CAT TTT AAC AAG ACA TTT GTC ACA GAG     347
Met Glu Phe Lys Leu Glu Glu His Phe Asn Lys Thr Phe Val Thr Glu
 1               5                  10                  15

AAC AAT ACA GCT GCT GCT CGG AAT GCA GCC TTC CCT GCC TGG GAG GAC     395
Asn Asn Thr Ala Ala Ala Arg Asn Ala Ala Phe Pro Ala Trp Glu Asp
             20                  25                  30

TAC AGA GGC AGC GTA GAC GAT TTA CAA TAC TTT CTG ATT GGG CTC TAT     443
Tyr Arg Gly Ser Val Asp Asp Leu Gln Tyr Phe Leu Ile Gly Leu Tyr
         35                  40                  45

ACA TTC GTA AGT CTT CTT GGC TTT ATG GGC AAT CTA CTT ATT TTA ATG     491
Thr Phe Val Ser Leu Leu Gly Phe Met Gly Asn Leu Leu Ile Leu Met
     50                  55                  60

GCT CTT ATG AAA AAG CGC AAT CAG AAG ACT ACA GTG AAC TTT CTC ATA     539
Ala Leu Met Lys Lys Arg Asn Gln Lys Thr Thr Val Asn Phe Leu Ile
 65                  70                  75                  80

GGC AAC CTG GCC TTC TCC GAC ATC TTG GTC GTC CTG TTT TGC TCC CCT     587
Gly Asn Leu Ala Phe Ser Asp Ile Leu Val Val Leu Phe Cys Ser Pro
                 85                  90                  95

TTC ACC CTG ACC TCT GTC TTG TTG GAT CAG TGG ATG TTT GGC AAA GTC     635
Phe Thr Leu Thr Ser Val Leu Leu Asp Gln Trp Met Phe Gly Lys Val
             100                 105                 110

ATG TGC CAT ATC ATG CCG TTC CTT CAA TGT GTG TCA GTT CTG GTT TCA     683
Met Cys His Ile Met Pro Phe Leu Gln Cys Val Ser Val Leu Val Ser
         115                 120                 125

ACT CTG ATT TTA ATA TCA ATT GCC ATT GTC AGG TAT CAT ATG ATA AAA     731
Thr Leu Ile Leu Ile Ser Ile Ala Ile Val Arg Tyr His Met Ile Lys
     130                 135                 140

CAT CCC ATA TCT AAT AAT TTA ACA GCA AAC CAT GGC TAC TTT CTG ATA     779
His Pro Ile Ser Asn Asn Leu Thr Ala Asn His Gly Tyr Phe Leu Ile
145                 150                 155                 160

GCT ACT GTC TGG ACA CTA GGT TTT GCC ATC TGT TCT CCC CTT CCA GTG     827
Ala Thr Val Trp Thr Leu Gly Phe Ala Ile Cys Ser Pro Leu Pro Val
                 165                 170                 175

TTT CAC AGT CTT GTG GAA CTT CAA GAA ACA TTT GGT TCA GCA TTG CTG     875
Phe His Ser Leu Val Glu Leu Gln Glu Thr Phe Gly Ser Ala Leu Leu
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     | 180 |     |     |     |     | 185 |     |     |     |     | 190 |     |      |
| AGC | AGC | AGG | TAT | TTA | TGT | GTT | GAG | TCA | TGG | CCA | TCT | GAT | TCA | TAC AGA | 923  |
| Ser | Ser | Arg | Tyr | Leu | Cys | Val | Glu | Ser | Trp | Pro | Ser | Asp | Ser | Tyr Arg |      |
|     |     | 195 |     |     |     |     | 200 |     |     |     |     | 205 |     |         |      |
| ATT | GCC | TTT | ACT | ATC | TCT | TTA | TTG | CTA | GTT | CAG | TAT | ATT | CTG | CCC TTA | 971  |
| Ile | Ala | Phe | Thr | Ile | Ser | Leu | Leu | Leu | Val | Gln | Tyr | Ile | Leu | Pro Leu |      |
|     |     | 210 |     |     |     |     | 215 |     |     |     |     | 220 |     |         |      |
| GTT | TGT | CTT | ACT | GTA | AGT | CAT | ACA | AGT | GTC | TGC | AGA | AGT | ATA | AGC TGT | 1019 |
| Val | Cys | Leu | Thr | Val | Ser | His | Thr | Ser | Val | Cys | Arg | Ser | Ile | Ser Cys |      |
| 225 |     |     |     |     | 230 |     |     |     |     | 235 |     |     |     | 240     |      |
| GGA | TTG | TCC | AAC | AAA | GAA | AAC | AGA | CTT | GAA | GAA | AAT | GAG | ATG | ATC AAC | 1067 |
| Gly | Leu | Ser | Asn | Lys | Glu | Asn | Arg | Leu | Glu | Glu | Asn | Glu | Met | Ile Asn |      |
|     |     |     |     | 245 |     |     |     |     | 250 |     |     |     |     | 255     |      |
| TTA | ACT | CTT | CAT | CCA | TCC | AAA | AAG | AGT | GGG | CCT | CAG | GTG | AAA | CTC TCT | 1115 |
| Leu | Thr | Leu | His | Pro | Ser | Lys | Lys | Ser | Gly | Pro | Gln | Val | Lys | Leu Ser |      |
|     |     |     | 260 |     |     |     |     | 265 |     |     |     |     | 270 |         |      |
| GGC | AGC | CAT | AAA | TGG | AGT | TAT | TCA | TTC | ATC | AAA | AAA | CAC | AGA | AGA AGA | 1163 |
| Gly | Ser | His | Lys | Trp | Ser | Tyr | Ser | Phe | Ile | Lys | Lys | His | Arg | Arg Arg |      |
|     |     | 275 |     |     |     |     | 280 |     |     |     |     | 285 |     |         |      |
| TAT | AGC | AAG | AAG | ACA | GCA | TGT | GTG | TTA | CCT | GCT | CCA | GAA | AGA | CCT TCT | 1211 |
| Tyr | Ser | Lys | Lys | Thr | Ala | Cys | Val | Leu | Pro | Ala | Pro | Glu | Arg | Pro Ser |      |
|     | 290 |     |     |     |     | 295 |     |     |     |     | 300 |     |     |         |      |
| CAA | GAG | AAC | CAC | TCC | AGA | ATA | CTT | CCA | GAA | AAC | TTT | GGC | TCT | GTA AGA | 1259 |
| Gln | Glu | Asn | His | Ser | Arg | Ile | Leu | Pro | Glu | Asn | Phe | Gly | Ser | Val Arg |      |
| 305 |     |     |     |     | 310 |     |     |     |     | 315 |     |     |     | 320     |      |
| AGT | CAG | CTC | TCT | TCA | TCC | AGT | AAG | TTC | ATA | CCA | GGG | GTC | CCC | ACT TGC | 1307 |
| Ser | Gln | Leu | Ser | Ser | Ser | Ser | Lys | Phe | Ile | Pro | Gly | Val | Pro | Thr Cys |      |
|     |     |     |     | 325 |     |     |     |     | 330 |     |     |     |     | 335     |      |
| TTT | GAG | ATA | AAA | CCT | GAA | GAA | AAT | TCA | GAT | GTT | CAT | GAA | TTG | AGA GTA | 1355 |
| Phe | Glu | Ile | Lys | Pro | Glu | Glu | Asn | Ser | Asp | Val | His | Glu | Leu | Arg Val |      |
|     |     |     | 340 |     |     |     |     | 345 |     |     |     |     | 350 |         |      |
| AAA | CGT | TCT | GTT | ACA | AGA | ATA | AAA | AAG | AGA | TCT | CGA | AGT | GTT | TTC TAC | 1403 |
| Lys | Arg | Ser | Val | Thr | Arg | Ile | Lys | Lys | Arg | Ser | Arg | Ser | Val | Phe Tyr |      |
|     |     | 355 |     |     |     |     | 360 |     |     |     |     | 365 |     |         |      |
| AGA | CTG | ACC | ATA | CTG | ATA | TTA | GTA | TTT | GCT | GTT | AGT | TGG | ATG | CCA CTA | 1451 |
| Arg | Leu | Thr | Ile | Leu | Ile | Leu | Val | Phe | Ala | Val | Ser | Trp | Met | Pro Leu |      |
|     | 370 |     |     |     |     | 375 |     |     |     |     | 380 |     |     |         |      |
| CAC | CTT | TTC | CAT | GTG | GTA | ACT | GAT | TTT | AAT | GAC | AAT | CTT | ATT | TCA AAT | 1499 |
| His | Leu | Phe | His | Val | Val | Thr | Asp | Phe | Asn | Asp | Asn | Leu | Ile | Ser Asn |      |
| 385 |     |     |     |     | 390 |     |     |     |     | 395 |     |     |     | 400     |      |
| AGG | CAT | TTC | AAG | TTG | GTG | TAT | TGC | ATT | TGT | CAT | TTG | TTG | GGC | ATG ATG | 1547 |
| Arg | His | Phe | Lys | Leu | Val | Tyr | Cys | Ile | Cys | His | Leu | Leu | Gly | Met Met |      |
|     |     |     |     | 405 |     |     |     |     | 410 |     |     |     |     | 415     |      |
| TCC | TGT | TGT | CTT | AAT | CCA | ATT | CTA | TAT | GGG | TTT | CTT | AAT | AAT | GGG ATT | 1595 |
| Ser | Cys | Cys | Leu | Asn | Pro | Ile | Leu | Tyr | Gly | Phe | Leu | Asn | Asn | Gly Ile |      |
|     |     |     | 420 |     |     |     |     | 425 |     |     |     |     | 430 |         |      |
| AAA | GCT | GAT | TTA | GTG | TCC | CTT | ATA | CAC | TGT | CTT | CAT | ATG | TAATAATTCT |  | 1644 |
| Lys | Ala | Asp | Leu | Val | Ser | Leu | Ile | His | Cys | Leu | His | Met |     |         |      |
|     |     | 435 |     |     |     |     | 440 |     |     |     |     | 445 |     |         |      |

CACTGTTTAC CAAGGAAAGA ACCTCGAG                                                                        1672

(2) INFORMATION FOR SEQ ID NO:2:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:2:

```
Met Glu Phe Lys Leu Glu Glu His Phe Asn Lys Thr Phe Val Thr Glu
 1               5                  10                  15

Asn Asn Thr Ala Ala Ala Arg Asn Ala Ala Phe Pro Ala Trp Glu Asp
            20                  25                  30

Tyr Arg Gly Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Leu Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Val
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
            180                 185                 190

Ser Ser Arg Tyr Leu Cys Val Glu Ser Trp Pro Ser Asp Ser Tyr Arg
        195                 200                 205

Ile Ala Phe Thr Ile Ser Leu Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Lys Lys Ser Gly Pro Gln Val Lys Leu Ser
            260                 265                 270

Gly Ser His Lys Trp Ser Tyr Ser Phe Ile Lys Lys His Arg Arg Arg
        275                 280                 285

Tyr Ser Lys Lys Thr Ala Cys Val Leu Pro Ala Pro Glu Arg Pro Ser
    290                 295                 300

Gln Glu Asn His Ser Arg Ile Leu Pro Glu Asn Phe Gly Ser Val Arg
305                 310                 315                 320

Ser Gln Leu Ser Ser Ser Lys Phe Ile Pro Gly Val Pro Thr Cys
                325                 330                 335

Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
        355                 360                 365

Arg Leu Thr Ile Leu Ile Leu Val Phe Ala Val Ser Trp Met Pro Leu
    370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
            420                 425                 430
```

```
Lys Ala Asp Leu Val Ser Leu Ile His Cys Leu His Met
435                 440                 445
```

(2) INFORMATION FOR SEQ ID NO:3:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

GGGCTCGAGG TTCTTTCCTT GGTAAACAGT GAG                      33

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GGGGGATCCT GACAAATGTC TTTTTATTCC AAG                      33

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGGCTCGAGG TTCTTTCCTT GGTAAACAGT GAG                      33

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

TTTGGATCCA CCATGGATTT AGAG                               24

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

TACCTGACAA TGGCAATTGA TATT                               24

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

TAATACGACT CACTATAGGG                                                   20

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

AAGGCATAAT ATGGCACATG AC                                           22

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

TAATACGACT CACTATAGGG                                                   20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

ACTTACAAAT GTATAGAGCC C                                             21

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGGCTCGAGG CACAGAGAGA ATCATGACAT GTG                           33

(2) INFORMATION FOR SEQ ID NO:13:

(i) SEQUENCE CHARACTERISTICS:
        (A) LENGTH: 33 base pairs
        (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO:13:

GGGGGATCCG CTGCTAATGG ACGTCCTCTT CTT                               33

(2) INFORMATION FOR SEQ ID NO:14:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:14:

GGGCTCGAGG CACAGAGAGA ATCATGACAT GTG                               33

(2) INFORMATION FOR SEQ ID NO:15:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:15:

TTTGGATCCA CCATGGAGTT TAAG                                         24

(2) INFORMATION FOR SEQ ID NO:16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:16:

AGGAAGTAGC CATGGTTTGC CGTT                                         24

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:17:

GGAGCAAAAC AGGACGAC                                                18

(2) INFORMATION FOR SEQ ID NO:18:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:18:

```
CGCGGATCCC CGAGGTGCTT CTAAAAC                                         27
```

(2) INFORMATION FOR SEQ ID NO:19:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
GGAGCAAAAC AGGACGAC                                                   18
```

(2) INFORMATION FOR SEQ ID NO:20:

(i) SEQUENCE CHARACTERISTICS:
        (A) LENGTH: 1633 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 261..1595

(xi) SEQUENCE DESCRIPTION: SEQ ID NO:20:

```
GGATCCGAAG GGGTTCGAAT TCCCCACCGC CGCCTCCAGG TCCTGCTCCC GCTGCTGCCG       60

CCACCGCCGG GGTGCAGGAG CGATCGCGCT GGGCCGCGCT CCCGGGAGCC CAGGGCCTGC      120

AGCGGCCGGG GCGCCCCGAG GTCTGCTCAT TGTGTTTTTC AGGAAAAAGG AAGGGAAAGG      180

GTGTTACAAG GAAAGGCTAT CGGTAACAAC TGACCTGCCA CAAAGTTAGA AGAAAGGATT      240

GATTCAAGAA AGACTATAAT ATG GAT TTA GAG CTC GAC GAG TAT TAT AAC         290
                        Met Asp Leu Glu Leu Asp Glu Tyr Tyr Asn
                          1               5                  10

AAG ACA CTT GCC ACA GAG AAT AAT ACT GCT GCC ACT CGG AAT TCT GAT        338
Lys Thr Leu Ala Thr Glu Asn Asn Thr Ala Ala Thr Arg Asn Ser Asp
             15                  20                  25

TTC CCA GTC TGG GAT GAC TAT AAA AGC AGT GTA GAT GAC TTA CAG TAT        386
Phe Pro Val Trp Asp Asp Tyr Lys Ser Ser Val Asp Asp Leu Gln Tyr
         30                  35                  40

TTT CTG ATT GGG CTC TAT ACA TTT GTA AGT CTT CTT GGC TTT ATG GGG        434
Phe Leu Ile Gly Leu Tyr Thr Phe Val Ser Leu Leu Gly Phe Met Gly
     45                  50                  55

AAT CTA CTT ATT TTA ATG GCT CTC ATG AAA AAG CGT AAT CAG AAG ACT        482
Asn Leu Leu Ile Leu Met Ala Leu Met Lys Lys Arg Asn Gln Lys Thr
 60                  65                  70

ACG GTA AAC TTC CTC ATA GGC AAT CTG GCC TTT TCT GAT ATC TTG GTT        530
Thr Val Asn Phe Leu Ile Gly Asn Leu Ala Phe Ser Asp Ile Leu Val
 75                  80                  85                  90

GTG CTG TTT TGC TCA CCT TTC ACA CTG ACG TCT GTC TTG CTG GAT CAG        578
Val Leu Phe Cys Ser Pro Phe Thr Leu Thr Ser Val Leu Leu Asp Gln
                 95                 100                 105

TGG ATG TTT GGC AAA GTC ATG TGC CAT ATT ATG CCT TTT CTT CAA TGT        626
Trp Met Phe Gly Lys Val Met Cys His Ile Met Pro Phe Leu Gln Cys
             110                 115                 120

GTG TCA GTT TTG GTT TCA ACT TTA ATT TTA ATA TCA ATT GCC ATT GTC        674
Val Ser Val Leu Val Ser Thr Leu Ile Leu Ile Ser Ile Ala Ile Val
         125                 130                 135
```

```
AGG TAT CAT ATG ATA AAA CAT CCC ATA TCT AAT AAT TTA ACA GCA AAC       722
Arg Tyr His Met Ile Lys His Pro Ile Ser Asn Asn Leu Thr Ala Asn
140                 145                 150

CAT GGC TAC TTT CTG ATA GCT ACT GTC TGG ACA CTA GGT TTT GCC ATC       770
His Gly Tyr Phe Leu Ile Ala Thr Val Trp Thr Leu Gly Phe Ala Ile
155                 160                 165                 170

TGT TCT CCC CTT CCA GTG TTT CAC AGT CTT GTG GAA CTT CAA GAA ACA       818
Cys Ser Pro Leu Pro Val Phe His Ser Leu Val Glu Leu Gln Glu Thr
                175                 180                 185

TTT GGT TCA GCA TTG CTG AGC AGC AGG TAT TTA TGT GTT GAG TCA TGG       866
Phe Gly Ser Ala Leu Leu Ser Ser Arg Tyr Leu Cys Val Glu Ser Trp
            190                 195                 200

CCA TCT GAT TCA TAC AGA ATT GCC TTT ACT ATC TCT TTA TTG CTA GTT       914
Pro Ser Asp Ser Tyr Arg Ile Ala Phe Thr Ile Ser Leu Leu Leu Val
        205                 210                 215

CAG TAT ATT CTG CCC TTA GTT TGT CTT ACT GTA AGT CAT ACA AGT GTC       962
Gln Tyr Ile Leu Pro Leu Val Cys Leu Thr Val Ser His Thr Ser Val
220                 225                 230

TGC AGA AGT ATA AGC TGT GGA TTG TCC AAC AAA GAA AAC AGA CTT GAA      1010
Cys Arg Ser Ile Ser Cys Gly Leu Ser Asn Lys Glu Asn Arg Leu Glu
235                 240                 245                 250

GAA AAT GAG ATG ATC AAC TTA ACT CTT CAT CCA TCC AAA AAG AGT GGG      1058
Glu Asn Glu Met Ile Asn Leu Thr Leu His Pro Ser Lys Lys Ser Gly
                255                 260                 265

CCT CAG GTG AAA CTC TCT GGC AGC CAT AAA TGG AGT TAT TCA TTC ATC      1106
Pro Gln Val Lys Leu Ser Gly Ser His Lys Trp Ser Tyr Ser Phe Ile
                270                 275                 280

AAA AAA CAC AGA AGA AGA TAT AGC AAG AAG ACA GCA TGT GTG TTA CCT      1154
Lys Lys His Arg Arg Arg Tyr Ser Lys Lys Thr Ala Cys Val Leu Pro
            285                 290                 295

GCT CCA GAA AGA CCT TCT CAA GAG AAC CAC TCC AGA ATA CTT CCA GAA      1202
Ala Pro Glu Arg Pro Ser Gln Glu Asn His Ser Arg Ile Leu Pro Glu
300                 305                 310

AAC TTT GGC TCT GTA AGA AGT CAG CTC TCT TCA TCC AGT AAG TTC ATA      1250
Asn Phe Gly Ser Val Arg Ser Gln Leu Ser Ser Ser Ser Lys Phe Ile
315                 320                 325                 330

CCA GGG GTC CCC ACT TGC TTT GAG ATA AAA CCT GAA GAA AAT TCA GAT      1298
Pro Gly Val Pro Thr Cys Phe Glu Ile Lys Pro Glu Glu Asn Ser Asp
                335                 340                 345

GTT CAT GAA TTG AGA GTA AAA CGT TCT GTT ACA AGA ATA AAA AAG AGA      1346
Val His Glu Leu Arg Val Lys Arg Ser Val Thr Arg Ile Lys Lys Arg
                350                 355                 360

TCT CGA AGT GTT TTC TAC AGA CTG ACC ATA CTG ATA TTA GTA TTT GCT      1394
Ser Arg Ser Val Phe Tyr Arg Leu Thr Ile Leu Ile Leu Val Phe Ala
            365                 370                 375

GTT AGT TGG ATG CCA CTA CAC CTT TTC CAT GTG GTA ACT GAT TTT AAT      1442
Val Ser Trp Met Pro Leu His Leu Phe His Val Val Thr Asp Phe Asn
        380                 385                 390

GAC AAT CTT ATT TCA AAT AGG CAT TTC AAG TTG GTG TAT TGC ATT TGT      1490
Asp Asn Leu Ile Ser Asn Arg His Phe Lys Leu Val Tyr Cys Ile Cys
395                 400                 405                 410

CAT TTG TTG GGC ATG ATG TCC TGT TGT CTT AAT CCA ATT CTA TAT GGG      1538
His Leu Leu Gly Met Met Ser Cys Cys Leu Asn Pro Ile Leu Tyr Gly
                415                 420                 425

TTT CTT AAT AAT GGG ATT AAA GCT GAT TTA GTG TCC CTT ATA CAC TGT      1586
Phe Leu Asn Asn Gly Ile Lys Ala Asp Leu Val Ser Leu Ile His Cys
                430                 435                 440

CTT CAT ATG TAATAATTCT CACTGTTTAC CAAGGAAAGA ACCTCGAG               1633
Leu His Met
445
```

(2) INFORMATION FOR SEQ ID NO:21:

(i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:21:

```
Met Asp Leu Glu Leu Asp Glu Tyr Tyr Asn Lys Thr Leu Ala Thr Glu
 1               5                  10                  15

Asn Asn Thr Ala Ala Thr Arg Asn Ser Asp Phe Pro Val Trp Asp Asp
             20                  25                  30

Tyr Lys Ser Ser Val Asp Asp Leu Gln Tyr Phe Leu Ile Gly Leu Tyr
         35                  40                  45

Thr Phe Val Ser Leu Leu Gly Phe Met Gly Asn Leu Leu Ile Leu Met
 50                  55                  60

Ala Leu Met Lys Lys Arg Asn Gln Lys Thr Thr Val Asn Phe Leu Ile
 65                  70                  75                  80

Gly Asn Leu Ala Phe Ser Asp Ile Leu Val Val Leu Phe Cys Ser Pro
                 85                  90                  95

Phe Thr Leu Thr Ser Val Leu Leu Asp Gln Trp Met Phe Gly Lys Val
                100                 105                 110

Met Cys His Ile Met Pro Phe Leu Gln Cys Val Ser Val Leu Val Ser
            115                 120                 125

Thr Leu Ile Leu Ile Ser Ile Ala Ile Val Arg Tyr His Met Ile Lys
130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Gln Glu Thr Phe Gly Ser Ala Leu Leu
                180                 185                 190

Ser Ser Arg Tyr Leu Cys Val Glu Ser Trp Pro Ser Asp Ser Tyr Arg
            195                 200                 205

Ile Ala Phe Thr Ile Ser Leu Leu Leu Val Gln Tyr Ile Leu Pro Leu
        210                 215                 220

Val Cys Leu Thr Val Ser His Thr Ser Val Cys Arg Ser Ile Ser Cys
225                 230                 235                 240

Gly Leu Ser Asn Lys Glu Asn Arg Leu Glu Glu Asn Glu Met Ile Asn
                245                 250                 255

Leu Thr Leu His Pro Ser Lys Lys Ser Gly Pro Gln Val Lys Leu Ser
            260                 265                 270

Gly Ser His Lys Trp Ser Tyr Ser Phe Ile Lys Lys His Arg Arg Arg
        275                 280                 285

Tyr Ser Lys Lys Thr Ala Cys Val Leu Pro Ala Pro Glu Arg Pro Ser
290                 295                 300

Gln Glu Asn His Ser Arg Ile Leu Pro Glu Asn Phe Gly Ser Val Arg
305                 310                 315                 320

Ser Gln Leu Ser Ser Ser Lys Phe Ile Pro Gly Val Pro Thr Cys
                325                 330                 335

Phe Glu Ile Lys Pro Glu Glu Asn Ser Asp Val His Glu Leu Arg Val
            340                 345                 350

Lys Arg Ser Val Thr Arg Ile Lys Lys Arg Ser Arg Ser Val Phe Tyr
        355                 360                 365
```

```
Arg Leu Thr Ile Leu Ile Leu Val Phe Ala Val Ser Trp Met Pro Leu
    370                 375                 380

His Leu Phe His Val Val Thr Asp Phe Asn Asp Asn Leu Ile Ser Asn
385                 390                 395                 400

Arg His Phe Lys Leu Val Tyr Cys Ile Cys His Leu Leu Gly Met Met
                405                 410                 415

Ser Cys Cys Leu Asn Pro Ile Leu Tyr Gly Phe Leu Asn Asn Gly Ile
                420                 425                 430

Lys Ala Asp Leu Val Ser Leu Ile His Cys Leu His Met
                435                 440                 445

(2) INFORMATION FOR SEQ ID NO:22:

(i) SEQUENCE CHARACTERISTICS:
        (A) LENGTH: 1655 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 300..1634

(xi) SEQUENCE DESCRIPTION: SEQ ID NO:22:
```

| | | |
|---|---|---|
| GGATCCCCGA GGTGCTTCTA AAACCCTGGC GGCTCCGGAG CCCCTCCTTC CCACCACCGC | 60 |
| CTCCAGGTCC TGCTCCTGCC GCCACCGCTT CCATCTGGAG CAGAAGCGAC CGCGCTCAGC | 120 |
| CACGTACCCC GGAGTCCAGG CACCCGCAGC GGCCGGGGCA TCCCGAGCTG GCCATACACC | 180 |
| GGGAGACAGC TGTGCCCTTG GGTTTGCAAG GTGGCTTGGA AGTCAACTGC CAGTAGGAAA | 240 |
| TAGCCATCCA CACACCTGAG TTCCAAGGGG GAAGAAAGAG ATTCTTATCT GATTCTAGT | 299 |

```
ATG GAG TTT AAG CTT GAG GAG CAT TTT AAC AAG ACA TTT GTC ACA GAG     347
Met Glu Phe Lys Leu Glu Glu His Phe Asn Lys Thr Phe Val Thr Glu
  1               5                  10                  15

AAC AAT ACA GCT GCT GCT CGG AAT GCA GCC TTC CCT GCC TGG GAG GAC     395
Asn Asn Thr Ala Ala Ala Arg Asn Ala Ala Phe Pro Ala Trp Glu Asp
              20                  25                  30

TAC AGA GGC AGC GTA GAC GAT TTA CAA TAC TTT CTG ATT GGG CTC TAT     443
Tyr Arg Gly Ser Val Asp Asp Leu Gln Tyr Phe Leu Ile Gly Leu Tyr
          35                  40                  45

ACA TTC GTA AGT CTT CTT GGC TTT ATG GGC AAT CTA CTT ATT TTA ATG     491
Thr Phe Val Ser Leu Leu Gly Phe Met Gly Asn Leu Leu Ile Leu Met
       50                  55                  60

GCT GTT ATG AAA AAG CGC AAT CAG AAG ACT ACA GTG AAC TTT CTC ATA     539
Ala Val Met Lys Lys Arg Asn Gln Lys Thr Thr Val Asn Phe Leu Ile
 65                  70                  75                  80

GGC AAC CTG GCC TTC TCC GAC ATC TTG GTC GTC CTG TTT TGC TCC CCT     587
Gly Asn Leu Ala Phe Ser Asp Ile Leu Val Val Leu Phe Cys Ser Pro
                 85                  90                  95

TTC ACC CTG ACC TCT GTC TTG TTG GAT CAG TGG ATG TTT GGC AAA GCC     635
Phe Thr Leu Thr Ser Val Leu Leu Asp Gln Trp Met Phe Gly Lys Ala
            100                 105                 110

ATG TGC CAT ATC ATG CCG TTC CTT CAA TGT GTG TCA GTT CTG GTT TCA     683
Met Cys His Ile Met Pro Phe Leu Gln Cys Val Ser Val Leu Val Ser
        115                 120                 125

ACT CTG ATT TTA ATA TCA ATT GCC ATT GTC AGG TAT CAT ATG ATA AAG     731
Thr Leu Ile Leu Ile Ser Ile Ala Ile Val Arg Tyr His Met Ile Lys
    130                 135                 140

CAC CCT ATT TCT AAC AAT TTA ACG GCA AAC CAT GGC TAC TTC CTG ATA     779
```

```
His Pro Ile Ser Asn Asn Leu Thr Ala Asn His Gly Tyr Phe Leu Ile
145                 150                 155                 160

GCT ACT GTC TGG ACA CTG GGC TTT GCC ATC TGT TCT CCC CTC CCA GTG          827
Ala Thr Val Trp Thr Leu Gly Phe Ala Ile Cys Ser Pro Leu Pro Val
                165                 170                 175

TTT CAC AGT CTT GTG GAA CTT AAG GAG ACC TTT GGC TCA GCA CTG CTG          875
Phe His Ser Leu Val Glu Leu Lys Glu Thr Phe Gly Ser Ala Leu Leu
            180                 185                 190

AGT AGC AAA TAT CTC TGT GTT GAG TCA TGG CCC TCT GAT TCA TAC AGA          923
Ser Ser Lys Tyr Leu Cys Val Glu Ser Trp Pro Ser Asp Ser Tyr Arg
        195                 200                 205

ATT GCT TTC ACA ATC TCT TTA TTG CTA GTG CAG TAT ATC CTG CCT CTA          971
Ile Ala Phe Thr Ile Ser Leu Leu Leu Val Gln Tyr Ile Leu Pro Leu
    210                 215                 220

GTA TGT TTA ACG GTA AGT CAT ACC AGC GTC TGC CGA AGC ATA AGC TGT         1019
Val Cys Leu Thr Val Ser His Thr Ser Val Cys Arg Ser Ile Ser Cys
225                 230                 235                 240

GGA TTG TCC CAC AAA GAA AAC AGA CTC GAA GAA AAT GAG ATG ATC AAC         1067
Gly Leu Ser His Lys Glu Asn Arg Leu Glu Glu Asn Glu Met Ile Asn
                245                 250                 255

TTA ACC CTA CAG CCA TCC AAA AAG AGC AGG AAC CAG GCA AAA ACC CCC         1115
Leu Thr Leu Gln Pro Ser Lys Lys Ser Arg Asn Gln Ala Lys Thr Pro
            260                 265                 270

AGC ACT CAA AAG TGG AGC TAC TCA TTC ATC AGA AAG CAC AGA AGG AGG         1163
Ser Thr Gln Lys Trp Ser Tyr Ser Phe Ile Arg Lys His Arg Arg Arg
        275                 280                 285

TAC AGC AAG AAG ACG GCC TGT GTC TTA CCC GCC CCA GCA GGA CCT TCC         1211
Tyr Ser Lys Lys Thr Ala Cys Val Leu Pro Ala Pro Ala Gly Pro Ser
    290                 295                 300

CAG GGG AAG CAC CTA GCC GTT CCA GAA AAT CCA GCC TCC GTC CGT AGC         1259
Gln Gly Lys His Leu Ala Val Pro Glu Asn Pro Ala Ser Val Arg Ser
305                 310                 315                 320

CAG CTG TCG CCA TCC AGT AAG GTC ATT CCA GGG GTC CCA ATC TGC TTT         1307
Gln Leu Ser Pro Ser Ser Lys Val Ile Pro Gly Val Pro Ile Cys Phe
                325                 330                 335

GAG GTG AAA CCT GAA GAA AGC TCA GAT GCT CAT GAG ATG AGA GTC AAG         1355
Glu Val Lys Pro Glu Glu Ser Ser Asp Ala His Glu Met Arg Val Lys
            340                 345                 350

CGT TCC ATC ACT AGA ATA AAA AAG AGA TCT CGA AGT GTT TTC TAC AGA         1403
Arg Ser Ile Thr Arg Ile Lys Lys Arg Ser Arg Ser Val Phe Tyr Arg
        355                 360                 365

CTG ACC ATA CTG ATA CTC GTG TTC GCC GTT AGC TGG ATG CCA CTC CAC         1451
Leu Thr Ile Leu Ile Leu Val Phe Ala Val Ser Trp Met Pro Leu His
    370                 375                 380

GTC TTC CAC GTG GTG ACT GAC TTC AAT GAT AAC TTG ATT TCC AAT AGG         1499
Val Phe His Val Val Thr Asp Phe Asn Asp Asn Leu Ile Ser Asn Arg
385                 390                 395                 400

CAT TTC AAG CTG GTA TAC TGC ATC TGT CAC TTG TTA GGC ATG ATG TCC         1547
His Phe Lys Leu Val Tyr Cys Ile Cys His Leu Leu Gly Met Met Ser
                405                 410                 415

TGT TGT CTA AAT CCG ATC CTA TAT GGT TTC CTT AAT AAT GGT ATC AAA         1595
Cys Cys Leu Asn Pro Ile Leu Tyr Gly Phe Leu Asn Asn Gly Ile Lys
            420                 425                 430

GCA GAC TTG AGA GCC CTT ATC CAC TGC CTA CAC ATG TCA TGATTCTCTC          1644
Ala Asp Leu Arg Ala Leu Ile His Cys Leu His Met Ser
        435                 440                 445

TGTGCCTCGA G                                                            1655

(2) INFORMATION FOR SEQ ID NO:23:
```

-continued

```
    (i) SEQUENCE CHARACTERISTICS:
        (A) LENGTH: 445 amino acids
        (B) TYPE: amino acid
        (D) TOPOLOGY: linear (ii) MOLECULE TYPE: protein (xi) SEQUENCE DESCRIPTION: SEQ ID NO:23:

Met Glu Phe Lys Leu Glu Glu His Phe Asn Lys Thr Phe Val Thr Glu
 1               5                  10                  15

Asn Asn Thr Ala Ala Ala Arg Asn Ala Ala Phe Pro Ala Trp Glu Asp
            20                  25                  30

Tyr Arg Gly Ser Val Asp Asp Leu Gln Tyr Phe Leu Ile Gly Leu Tyr
        35                  40                  45

Thr Phe Val Ser Leu Leu Gly Phe Met Gly Asn Leu Leu Ile Leu Met
    50                  55                  60

Ala Val Met Lys Lys Arg Asn Gln Lys Thr Thr Val Asn Phe Leu Ile
65                  70                  75                  80

Gly Asn Leu Ala Phe Ser Asp Ile Leu Val Val Leu Phe Cys Ser Pro
                85                  90                  95

Phe Thr Leu Thr Ser Val Leu Leu Asp Gln Trp Met Phe Gly Lys Ala
            100                 105                 110

Met Cys His Ile Met Pro Phe Leu Gln Cys Val Ser Val Leu Val Ser
        115                 120                 125

Thr Leu Ile Leu Ile Ser Ile Ala Ile Val Arg Tyr His Met Ile Lys
    130                 135                 140

His Pro Ile Ser Asn Asn Leu Thr Ala Asn His Gly Tyr Phe Leu Ile
145                 150                 155                 160

Ala Thr Val Trp Thr Leu Gly Phe Ala Ile Cys Ser Pro Leu Pro Val
                165                 170                 175

Phe His Ser Leu Val Glu Leu Lys Glu Thr Phe Gly Ser Ala Leu Leu
            180                 185                 190

Ser Ser Lys Tyr Leu Cys Val Glu Ser Trp Pro Ser Asp Ser Tyr Arg
        195                 200                 205

Ile Ala Phe Thr Ile Ser Leu Leu Val Gln Tyr Ile Leu Pro Leu
    210                 215                 220

Val Cys Leu Thr Val Ser His Thr Ser Val Cys Arg Ser Ile Ser Cys
225                 230                 235                 240

Gly Leu Ser His Lys Glu Asn Arg Leu Glu Glu Asn Glu Met Ile Asn
                245                 250                 255

Leu Thr Leu Gln Pro Ser Lys Lys Ser Arg Asn Gln Ala Lys Thr Pro
            260                 265                 270

Ser Thr Gln Lys Trp Ser Tyr Ser Phe Ile Arg Lys His Arg Arg Arg
        275                 280                 285

Tyr Ser Lys Lys Thr Ala Cys Val Leu Pro Ala Pro Ala Gly Pro Ser
    290                 295                 300

Gln Gly Lys His Leu Ala Val Pro Glu Asn Pro Ala Ser Val Arg Ser
305                 310                 315                 320

Gln Leu Ser Pro Ser Ser Lys Val Ile Pro Gly Val Pro Ile Cys Phe
                325                 330                 335

Glu Val Lys Pro Glu Glu Ser Ser Asp Ala His Glu Met Arg Val Lys
            340                 345                 350

Arg Ser Ile Thr Arg Ile Lys Lys Arg Ser Arg Ser Val Phe Tyr Arg
        355                 360                 365

Leu Thr Ile Leu Ile Leu Val Phe Ala Val Ser Trp Met Pro Leu His
    370                 375                 380
```

```
Val Phe His Val Val Thr Asp Phe Asn Asp Asn Leu Ile Ser Asn Arg
385                 390                 395                 400

His Phe Lys Leu Val Tyr Cys Ile Cys His Leu Leu Gly Met Met Ser
            405                 410                 415

Cys Cys Leu Asn Pro Ile Leu Tyr Gly Phe Leu Asn Asn Gly Ile Lys
            420                 425                 430

Ala Asp Leu Arg Ala Leu Ile His Cys Leu His Met Ser
            435                 440                 445
```

CHIMERIC MAMMALIAN NPY Y$_5$ RECEPTORS

TECHNICAL FIELD

The present invention relates to mammalian neuropeptide Y (NPY) receptors. More particularly, it relates to chimeric mammalian NPY Y$_5$ receptors, nucleic acids and vectors encoding the receptors, methods for making the receptors, fragments or fusion proteins thereof using recombinant DNA methodology or chemical synthesis, and to methods for using the receptors in screening systems to identify compounds for the treatment of various diseases.

BACKGROUND OF THE INVENTION

Neuropeptide Y (NPY) is a 36 amino acid peptide that is widely distributed in both the central and peripheral nervous systems (1). As might be expected from its widespread distribution, NPY has a plethora of physiological actions, including effects on blood pressure, hormone release, gut motility, smooth muscle tone, sleep and circadian rhythms, feeding, thermogenesis, neuronal excitability, nociception, cognition, mood and emotional responses. NPY mediates these physiological effects via interaction with at least six distinct G protein-coupled receptors (designated Y$_1$–Y$_6$) (2). It is possible that additional NPY receptors remain to be cloned and characterized. Available data indicate that the NPY Y$_5$ receptor mediates the effects of NPY on feeding, thermogenesis, neuronal excitability and seizure activity, diuresis, natriuresis and calciuresis (3,4,5).

Several lines of evidence suggest that NPY plays a key role in the control of body weight. Central administration of NPY increases food intake and decreases thermogenesis in satiated animals while reductions in endogenous NPY via antisense oligonucleotide or immunoneutralization techniques leads to a decrease in food intake (1,6,7). As would be expected for an orexigenic peptide, hypothalamic NPY peptide and mRNA levels are increased after fasting and in genetically obese mice (8). In fact, recent experiments with transgenic mice lacking NPY indicate that NPY is required for the maintenance of the obese phenotype of ob/ob mice (9). Conversely, the satiety signal leptin appears to decrease food intake and body weight in part by decreasing NPY synthesis and release (10). The pharmacological properties of the Y$_5$ receptor subtype most closely match the pharmacological properties of the receptor mediating the effects of NPY on feeding (3). These data suggest that NPY is a key modulator of body weight and that NPY Y$_5$ receptor antagonists will be useful anti-obesity agents.

NPY has also been shown to block kainic acid-induced seizures in rats, suggesting that NPY may be a potent anti-epileptic agent (4). The pharmacological properties of the receptor that mediate the anti-epileptic effects of NPY are similar to the pharmacological properties of the Y$_5$ receptor (4). Therefore, NPY Y$_5$ receptor agonists may be useful anti-epileptic agents.

NPY also elicits a diuretic, natriuretic and calciuretic effect in the kidney (5). Again, the pharmacological properties of the receptor that mediates these effects are similar to the pharmacological properties of the Y$_5$ receptor (5). It is conceivable, therefore, that NPY Y$_5$ receptor agonists would be effective anti-hypertensive agents and/or useful in the treatment of disorders of calcium metabolism.

NPY has numerous physiological effects which cannot yet be conclusively ascribed to a particular NPY receptor subtype (1). It is certainly possible that some of these effects are due to interaction of NPY with the Y$_5$ receptor. The involvement of NPY in sleep and other circadian rhythms suggests that Y$_5$ receptor agonists might be useful in the treatment of sleep disorders, including jet lag. The known effects of NPY on hormone release suggest that Y$_5$ agonists or antagonists might be useful as contraceptives or in the treatment of infertility or sexual dysfunction. NPY also regulates vascular tone in cerebral vessels, suggesting that Y$_5$ agonists or antagonists might have value in the treatment of migraine. Since NPY is also known to be involved in the transmission of painful stimuli, Y$_5$ agonists or antagonists might be useful analgesics. NPY has also been shown to have effects on cognitive processes and, hence, Y$_5$ receptor agonists or antagonists might be effective cognition-enhancing agents. Disorders of gut motility could also be treated with a Y$_5$ agonist or antagonist. NPY itself is also anxiolytic and, thus, Y$_5$ receptor agonists might be useful anxiolytic agents. Finally, NPY is localized in brain regions that play a role in affective disorders, suggesting that Y$_5$ ligands could be useful antidepressants or antipsychotic agents.

The present inventors have isolated cDNAs encoding the rat and human NPY Y$_5$ receptors and used those nucleic acids to construct a novel chimeric cDNA construct that enables high levels of human NPY Y$_5$ receptor expression.

U.S. Pat. No. 5,603,024 ('024 patent) refers to isolated cDNAs encoding human and rat NPY Y$_5$ receptors. The cDNA sequences disclosed in the '024 patent, however, differ from the sequences of the cDNAs isolated by the present inventors and used in the construction of the novel chimeric receptor cDNA.

For example, the sequences of the human NPY Y$_5$ receptor isolated by the present inventors and that disclosed in the '024 patent diverge prior to nucleotide number 82 of the '024 sequence. The net result of this divergence is that the translated human NPY Y$_5$ receptor protein encoded by the '024 patent cDNA has 10 additional amino acids at the amino terminus relative to the translated protein encoded by the human cDNA isolated by the present inventors. Sequencing of the human NPY Y$_5$ receptor gene reveals that the sequence disclosed in the '024 patent is in reality a genomic sequence.

Likewise, sequence analysis indicates that the rat NPY Y$_5$ receptor cDNA sequence disclosed in the '024 patent is in fact a genomic sequence.

Similar conclusions were drawn in the recently published International Application WO 97/17440.

In view of the important role of the NPY Y$_5$ receptor in many physiological processes and medical conditions, there is a need for materials and methods for identifying selective agonists and antagonists of the NPY Y$_5$ receptor.

SUMMARY OF THE INVENTION

The present invention fills the foregoing need by providing such materials and methods. More particularly, this invention provides novel chimeric mammalian NPY Y$_5$ receptors, nucleic acids encoding the receptors, and recombinant vectors and host cells comprising such nucleic acids.

The nucleic acids are selected from the group consisting of:

(a) a nucleic acid encoding a chimeric mammalian NPY Y$_5$ receptor comprising an amino acid sequence defined by SEQ ID NO: 2 or a conservative or allelic variant thereof;

(b) a nucleic acid that hybridizes under moderately stringent conditions to the nucleic acid of (a) and encodes a polypeptide that (i) binds NPY and (ii) is at least 80% identical to a receptor encoded by the nucleic acid of (a); and (c) a nucleic acid that, due to the degeneracy of the genetic code, encodes a chimeric mammalian NPY $Y_5$ receptor encoded by a nucleic acid of (a) or (b).

This invention further provides a method for producing a chimeric mammalian NPY $Y_5$ receptor comprising culturing a host cell comprising a nucleic acid encoding a mammalian NPY $Y_5$ receptor comprising an amino acid sequence defined by SEQ ID NO: 2 or a conservative or allelic variant thereof, under conditions in which the nucleic acid is expressed. In one embodiment the receptor is isolated from the culture.

The present invention also provides a method for identifying a NPY $Y_5$ agonist or antagonist comprising:

(a) contacting a chimeric mammalian NPY $Y_5$ receptor having an amino acid sequence defined by SEQ ID NO: 2 or a conservative or allelic variant thereof, in the presence of a known amount of labeled NPY with a sample to be tested for the presence of a NPY $Y_5$ agonist or antagonist; and (b) measuring the amount of labeled NPY specifically bound to the receptor;

whereby a NPY $Y_5$ agonist or antagonist in the sample is identified by measuring substantially reduced binding of the labeled NPY to the NPY $Y_5$ receptor, compared to what would be measured in the absence of such agonist or antagonist.

The present invention further provides a functional assay for identifying receptor NPY $Y_5$ agonists or anatagonists comprsing:

(a) contacting cells expressing a chimeric mammalian NPY $Y_5$ receptor having an amino acid sequence defined by SEQ ID NO: 2 in the presence of a known amount of forskolin with a sample to be tested for the presence of a NPY $Y_5$ agonist or antagonist; and (b) measuring the amount of cyclic AMP (cAMP) present in the cells;

whereby a NPY $Y_5$ agonist or antagonist in the sample is identified by measuring its effect on the forskolin-stimulated cAMP accumulation in cells expressing a chimeric mammalian NPY $Y_5$ receptor, compared to what would be measured in the absence of such agonist or antagonist.

In a preferred embodiment, membranes isolated from mammalian cells comprising a nucleic acid encoding the chimeric NPY $Y_5$ receptor are used as the source of the receptor.

This invention still further provides a method for treating NPY $Y_5$ receptor-mediated medical conditions comprising administering to a mammal afflicted with a medical condition caused or mediated by NPY $Y_5$ receptor, an effective amount of an agonist or an antagonist of the NPY $Y_5$ receptor.

DESCRIPTION OF THE INVENTION

All references cited herein are hereby incorporated herein in their entirety by reference.

As used herein, the term "ligand" is defined to mean any molecule capable of specifically binding to the mammalian NPY $Y_5$ receptors of the invention. Thus NPY itself is a ligand, as are agonists and antagonists that may compete with NPY for specific binding to the NPY $Y_5$ receptors.

The term "analog(s)" means a chimeric mammalian NPY $Y_5$ receptor of the invention which has been modified by deletion, addition, modification or substitution of one or more amino acid residues.

Some amino acid substitutions are preferably "conservative", with residues replaced with physicochemically similar residues, such as Gly/Ala, Asp/Glu, Val/Ile/Leu, Lys/Arg, Asn/Gln and Phe/Trp/Tyr. Analogs having such conservative substitutions typically retain substantial NPY $Y_5$ binding activity. Other analogs, which have non-conservative substitutions such as Asn/Glu, Val/Tyr and His/Glu, may substantially lack such activity. Nevertheless, such analogs are useful because they can be used as antigens to elicit production of antibodies in an immunologically competent host. Because these analogs retain many of the epitopes (antigenic determinants) of the wild-type receptors from which they are derived, many antibodies produced against them can also bind to the active-conformation or denatured wild-type receptors. Accordingly, such antibodies can also be used, e.g., for the immunopurification or immunoassay of the wild-type receptors.

Some analogs are truncated variants in which residues have been successively deleted from the amino- and/or carboxyl-termini, while substantially retaining the characteristic ligand binding activity.

Modifications of amino acid residues may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Other analogs are chimeric mammalian NPY $Y_5$ receptors containing modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Analogs of the chimeric mammalian NPY $Y_5$ receptors can be prepared by chemical synthesis or by using site-directed mutagenesis [Gillman et al., *Gene* 8:81 (1979); Roberts et al., *Nature* 328:731 (1987) or Innis (Ed.), 1990, *PCR Protocols: A Guide to Methods and Applications*, Academic Press, New York, N.Y.] or the polymerase chain reaction method [PCR; Saiki et al., *Science* 239:487 (1988)], as exemplified by Daugherty et al. [*Nucleic Acids Res.* 19:2471 (1991)] to modify nucleic acids encoding the complete receptors. Adding epitope tags for purification or detection of recombinant products is envisioned.

General techniques for nucleic acid manipulation and expression that can be used to make the analogs are described generally, e.g., in Sambrook, et al., *Molecular Cloning: A Laboratory Manual* (2d ed.), 1989, Vols. 1–3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et al., *Solid Phase Peptide Synthesis: A Practical Approach*, 1989, IRL Press, Oxford.

Still other analogs are prepared by the use of agents known in the art for their usefulness in cross-linking proteins through reactive side groups. Preferred derivatization sites with cross-linking agents are free amino groups, carbohydrate moieties and cysteine residues.

Protein Purification

The proteins, polypeptides and antigenic fragments of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology*, Vol. 182, M. Deutscher, Ed., 1990, Academic Press, New York, N.Y. More specific methods applicable to purification of the NPY Y$_5$ receptors are described below.

Purification steps can be followed by carrying out assays for ligand binding activity as described below. Particularly where a receptor is being isolated from a cellular or tissue source, it is preferable to include one or more inhibitors of proteolytic enzymes is the assay system, such as phenyl-methanesulfonyl fluoride (PMSF).

Nucleic Acids and Expression Vectors

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments not naturally contiguous to each other. Engineered vectors are encompassed, as well as nucleic acids comprising sequences derived using any synthetic oligonucleotide process.

For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the target of such artificial manipulations, other site-specific targets, e.g., promoters, DNA replication sites, regulation sequences, control sequences, or other useful features may be incorporated by design. Sequences encoding epitope tags for detection or purification as described above may also be incorporated.

A nucleic acid "fragment" is defined herein as a nucleotide sequence comprising at least about 17, generally at least about 25, preferably at least about 35, more preferably at least about 45, and most preferably at least about 55 or more contiguous nucleotides.

This invention further encompasses recombinant DNA molecules and fragments having sequences that are identical or highly homologous to those described herein. The nucleic acids of the invention may be operably linked to DNA segments which control transcription, translation, and DNA replication.

"Homologous nucleic acid sequences" are those which when aligned and compared exhibit significant similarities. Standards for homology in nucleic acids are either measures for homology generally used in the art by sequence comparison or based upon hybridization conditions, which are described in greater detail below.

Substantial nucleotide sequence homology is observed when there is identity in nucleotide residues in two sequences (or in their complementary strands) when optimally aligned to account for nucleotide insertions or deletions, in at least about 50%, preferably in at least about 75%, more preferably in at least about 90%, and most preferably in at least about 95% of the aligned nucleotides.

Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12:203 (1984).

The lengths of such homology comparisons may encompass longer stretches and in certain embodiments may cover a sequence of at least about 17, preferably at least about 25, more preferably at least about 50, and most preferably at least about 75 nucleotide residues.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., *J. Mol. Biol.* 31:349 (1968).

The term "substantially pure" is defined herein to mean a mammalian NPY Y$_5$ receptor, nucleic acid or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

Nucleic acids encoding the NPY Y$_5$ receptors or fragments thereof can be prepared by standard methods. For example, DNA can be chemically synthesized using, e.g., the phosphoramidite solid support method of Matteucci et al. [*J. Am. Chem. Soc.* 103:3185 (1981)], the method of Yoo et al. [*J. Biol. Chem.* 764:17078 (1989)], or other well known methods. This can be done by sequentially linking a series of oligonucleotide cassettes comprising pairs of synthetic oligonucleotides, as described below.

Of course, due to the degeneracy of the genetic code, many different nucleotide sequences can encode the NPY Y$_5$ receptors. The codons can be selected for optimal expression in prokaryotic or eukaryotic systems. Such degenerate variants are of course also encompassed by this invention.

Moreover, nucleic acids encoding the NPY Y$_5$ receptors can readily be modified by nucleotide substitutions, nucleotide deletions, nucleotide insertions, and inversions of nucleotide stretches. Such modifications result in novel DNA sequences which encode antigens having immunogenic or antigenic activity in common with the wild-type receptors. These modified sequences can be used to produce wild-type or mutant receptors, or to enhance expression in a recombinant DNA system.

Insertion of the DNAs encoding the NPY $Y_5$ receptors into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et al., *Science* 239:487 (1988). The cleaved vector and the DNA fragments may also be modified if required by homopolymeric tailing.

Recombinant expression vectors used in this invention are typically self-replicating DNA or RNA constructs comprising nucleic acids encoding one of the receptors, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles which may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

Expression of nucleic acids encoding the NPY $Y_5$ receptors of this invention can be carried out by conventional methods in either prokaryotic or eukaryotic cells. Although strains of *E, coli* are employed most frequently in prokaryotic systems, many other bacteria such as various strains of Pseudomonas and Bacillus are know in the art and can be used as well.

Prokaryotic expression control sequences typically used include promoters, including those derived from the b-lactamase and lactose promoter systems [Chang et al., *Nature* 198:1056 (1977)], the tryptophan (trp) promoter system [Goeddel et al., *Nucleic Acids Res.* 8:4057 (1980)], the lambda $P_L$ promoter system [Shimatake et al., *Nature* 292:128 (1981)] and the tac promoter [De Boer et al., *Proc. Natl. Acad. Sci.* USA 292:128 (1983)]. Numerous expression vectors containing such control sequences are known in the art and available commercially.

Suitable host cells for expressing nucleic acids encoding the receptors include prokaryotes and higher eukaryotes. Prokaryotes include both gram negative and positive organisms, e.g., *E. coli* and *B. subtiles*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptors include but are not limited to those containing the lac promoter (pUC-series); trp promoter (pBR322-trp); Ipp promoter (the pIN-series); lambda-pP or pR promoters (pOTS); or hybrid promoters such as ptac (pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses*, 1988, Buttersworth, Boston, pp. 205–236.

Higher eukaryotic tissue culture cells are preferred hosts for the recombinant production of the receptors. Although any higher eukaryotic tissue culture cell line might be used, including insect baculovirus expression systems, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR®3.1, pCDNA3.1, pClneo, pCD [Okayama et al., *Mol. Cell Biol.* 5:1136 (1985)], pMC1neo Poly-A [Thomas et al., *Cell*51:503 (1987)], pREP8, pSVSPORT and derivatives thereof, and baculovirus vectors such as pVL1392, pVL1393, pAcMP2 or pAcMP3.

Screening Systems and Methods

The NPY $Y_5$ receptors of this invention can be employed in screening systems to identify agonists or antagonists of the receptors. Essentially, these systems provide methods for bringing together a mammalian NPY $Y_5$ receptor, an appropriate known ligand, including NPY itself, and a sample to be tested for the presence of a NPY $Y_5$ agonist or antagonist.

Two basic types of screening systems can be used, a labeled-ligand binding assay and a "functional" assay. A labeled ligand for use in the binding assay can be obtained by labeling NPY or a known NPY $Y_5$ agonist or antagonist with a measurable group. In an example below, $^{125}$I-porcine peptide YY (PYY) is used as the ligand.

Typically, a given amount of one of the NPY $Y_5$ receptors of the invention is contacted with increasing amounts of a labeled ligand, and the amount of the bound labeled ligand is measured after removing unbound labeled ligand by washing. As the amount of the labeled ligand is increased, a point is eventually reached at which all receptor binding sites are occupied or saturated. Specific receptor binding of the labeled ligand is abolished by a large excess of unlabled ligand.

Preferably, an assay system is used in which non-specific binding of the labeled ligand to the receptor is minimal. Non-specific binding is typically less than 25%, preferably less than 15%, and more preferably less than 10% of the total binding of the labeled ligand.

The amino acid sequence of NPY is conserved among various species, including humans. Therefore, NPY from one species may bind to NPY $Y_5$ receptors from another species; e.g., porcine NPY binds to the rat receptor, as is illustrated in an Example below. For regulatory purposes, however, it may be desirable to use human NPY or an active fragment thereof as the NPY $Y_5$ ligand in conjunction with the human receptor when screening for NPY $Y_5$ receptor agonists or antagonists for human therapeutic purposes.

In principle, a binding assay of the invention could be carried out using a soluble receptor of the invention, e.g., following production and refolding by standard methods from an *E. coli* expression system, and the resulting receptor-labeled ligand complex could be precipitated, e.g., using an antibody against the receptor. The precipitate could then be washed and the amount of the bound labeled ligand could be measured.

Preferably, however, a nucleic acid encoding one of the NPY $Y_5$ receptors of the invention is transfected into an appropriate host cell, whereby the receptor will become incorporated into the membrane of the cell. A membrane fraction can then be isolated from the cell and used as a source of the receptor for assay. Preferably, binding of the labeled ligand to a membrane fraction from the untransfected host cell will be negligible, as is the case with COS-7 cells used in an Example below.

The binding assays of this invention can be used to identify both NPY $Y_5$ receptor agonists and antagonists, because both will compete for binding to the receptor with the labeled ligand.

In the basic binding assay, the method for identifying a NPY $Y_5$ receptor agonist or antagonist comprises:
  (a) contacting a mammalian NPY $Y_5$ receptor having an amino acid sequence defined by SEQ ID NO: 2 or a conservative or allelic variant thereof, in the presence of a known amount of labled NPY with a sample to be tested for the presence of a NPY $Y_5$ receptor agonist or antagonist; and
  (b) measuring the amount of labeled NPY bound to the receptor;
whereby a NPY $Y_5$ receptor agonist or antagonist in the sample is identified by measuring substantially reduced binding of the labeled NPY to the receptor, compared to what would be measured in the absence of such agonist or antagonist.

The present invention further provides a functional assay for identifying receptor NPY $Y_5$ agonists or anatagonists comprsing:
  (a) contacting cells expressing a chimeric mammalian NPY $Y_5$ receptor having an amino acid sequence defined by SEQ ID NO: 2 or a conservative or allelic variant thereof, in the presence of a known amount of forskolin with a sample to be tested for the presence of a NPY $Y_5$ agonist or antagonist; and
  (b) measuring the amount of cyclic AMP (cAMP) present in the cells;
whereby a NPY $Y_5$ agonist or antagonist in the sample is identified by measuring its effect on the forskolin-stimulated cAMP accumulation in cells expressing a chimeric mammalian NPY $Y_5$ receptor, compared to what would be measured in the absence of such agonist or antagonist.

The functional assay is based on the observation that NPY decreases forskolin-stimulated cAMP accumulation in cells expressing the NPY $Y_5$ receptor. Antagonists are identified by determining their ability to block the inhibition of forskolin-stimulated cAMP activity elicited by NPY. Agonists are identified by their ability to decrease forskolin-stimulated cAMP accumulation in cells expressing the NPY $Y_5$ receptor.

EXAMPLES

The present invention can be illustrated by the following examples. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and Methods

Restriction and modification enzymes were obtained from New England Biolabs (Beverly, Mass.), Promega (Madison, Wis.) or Life Technologies (Gaithersburg, Md.).

Standard methods were used, as described, e.g., in Maniatis et al., *Molecular Cloning: A Laboratory Manual*, 1982, Cold Spring Harbor Laboratory, Cold Spring Harbor Press; Sambrook et al., *Molecular Cloning: A Laboratory Manual*, (2d ed.), Vols 1–3, 1989, Cold Spring Harbor Press, NY; Ausubel et al., *Biology*, Greene Publishing Associates, Brooklyn, NY; or Ausubel, et al. (1987 and Supplements), *Current Protocols in Molecular Biology*, Greene/Wiley, New York; Innis et al. (eds.) *PCR Protocols: A Guide to Methods and Applications*, 1990, Academic Press, N.Y.

Isolation of the Human NPY $Y_5$ Receptor cDNA

Total RNA was isolated from the SK-N-MC human neuroblastoma cell line (American Type Culture Collection, Rockville, Md.) with the Tri Reagent kit (Molecular Research Center, Cincinnati, Ohio) according to the manufacturer's instructions. Poly $A^+$ RNA was isolated from SK-N-MC cell total RNA with the Fast Track 2.0 kit (InVitrogen, San Diego, Calif.) according to the manufacturer's instructions. SK-N-MC cell cDNA was prepared by reverse transcription with the GeneAmp RNA PCR Kit (Perkin Elmer, Norwalk, Conn.). Reverse transcription was performed in a 20 ul reaction mixture containing 4.56 ug of SK-N-MC cell poly $A^+$ RNA; 10 mM Tris-Cl (pH 8.3); 5 mM $MgCl_2$; 50 mM KCl; 1 mM each of dATP, dCTP, dTTP and dGTP; 1 U RNase inhibitor; 2.5 U murine Moloney leukemia virus reverse transcriptase; and 0.15 uM oligonucleotide primer having the sequence GGGCTCGAGGT-TCTTTCCTTGGTAAACAGTGAG (SEQ ID NO: 3). Nucleotides 10–33 of this primer correspond to nucleotides 1434–1457 of the sequence reported by Gerald et al. in U.S. Pat. No. 5,602,024 while nucleotides 14–33 of this primer correspond to nucleotides 1399–1418 of the sequence deposited by Gerald et al. in GenBank under accession number U56079. The reverse transcription mixture was placed in a Perkin Elmer 9600 thermocycler and subjected to one cycle of 42° C. for 15 minutes, 99° C. for 5 minutes and 5° C. for 5 minutes.

The human NPY $Y_5$ receptor cDNA was isolated from SK-N-MC cell cDNA by the polymerase chain reaction (PCR). The components of the PCR reaction were 10 mM Tris Cl (pH 8.3), 2 mM $MgCl_2$, 50 mM KCl, 2 ul of SK-N-MC cell cDNA from the reverse transcription reaction and 15 pmol of the oligonucleotide primers GGGGGATC-CTGACAAATGTCTTTTTATTCCAAG (sense primer) (SEQ ID NO: 4) and GGGCTCGAGGTTCTTTCCTTGG-TAAACAGTGAG (antisense primer) (SEQ ID NO: 5). Nucleotides 10–33 of the sense primer correspond to nucleotides 55–78 of the sequence reported by Gerald et al. in U.S. Pat. No. 5,602,024 and to nucleotides 20–43 of the sequence deposited by Gerald et al. in GenBank under accession number U56079. Nucleotides 10–33 of the antisense primer correspond to nucleotides 1434–1457 of the sequence reported by Gerald et al. in U.S. Pat. No. 5,602,024 while nucleotides 14–33 of the antisense primer correspond to nucleotides 1399–1418 of the sequence deposited by Gerald et al. in GenBank under accession number U56079. The PCR reaction was initially denatured at 94° C. for 1 minute. The PCR was then carried out for 35 cycles with each cycle of PCR consisting of denaturation at 94° C. for 30 seconds, annealing at 59° C. for 30 seconds, and elongation at 72° C. for 30 seconds. Subsequently, a final cycle of elongation was performed at 72° C. for 7 minutes. The reaction was then held at 4° C. until use. A 1402 bp product flanked by 5' BamHI and 3' XhoI restriction enzyme sites was obtained in this PCR reaction and was confirmed by DNA sequence analysis to incorporate nucleotides 55–1457 of the sequence reported by Gerald et al in U.S. Pat. No. 5,602,024 and nucleotides 20–1418 of the sequence deposited by Gerald et al. in GenBank under accession number U56079. This 1402 bp product was ligated into the plasmid pCR3.1 (InVitrogen) to yield a construct known as pCR3.1-hY$_{5A}$. When transfected into COS1 cells, this construct did not yield detectable expression of the human Y$_5$ receptor (Table 1).

Examination of the sequence of the 1402 bp human NPY Y$_5$ receptor cDNA and the sequences reported by Gerald et al. in U.S. Pat. No. 5,602,024 and GenBank accession number U56079 revealed that there were two in frame initiation codons at the 5' end of the cDNA. In an effort to improve expression of the human NPY Y$_5$ receptor, the 1402 bp human NPY Y$_5$ receptor cDNA was modified to remove the first initiation codon and the intervening nucleotides between the first and second initiation codons. In addition, a Kozak consensus sequence was added to improve expression. This was accomplished by PCR in which 100 ng of pCR3.1-hY$_{5A}$ was used as the template along with the oligonucleotide primers TTTGGATCCACCATGGATTTAGAG (sense primer) (SEQ ID NO: 6) and TACCTGACAATGGCAATTGATATT (antisense primer) (SEQ ID NO: 7). Nucleotides 13–24 of the sense primer correspond to nucleotides 91–102 of the sequence reported by Gerald et al. in U.S. Pat. No. 5,602,024 and to nucleotides 56–67 of the sequence deposited by Gerald et al. in GenBank under accession number U56079. The antisense primer corresponds to nucleotides 486–509 of the sequence reported by Gerald et al. in U.S. Pat. No. 5,602,024 and to nucleotides 451–474 of the sequence deposited by Gerald et al. in GenBank under accession number U56079. The PCR reaction was initially denatured at 94° C. for 1 minute. The PCR was then carried out for 35 cycles with each cycle of PCR consisting of denaturation at 94° C. for 45 seconds, annealing at 53° C. for 45 seconds, and elongation at 72° C. for 1 minute. Subsequently, a final cycle of elongation was performed at 72° C. for 7 minutes. The reaction was then held at 4° C. until use. This PCR reaction yielded a 419 bp product that incorporated nucleotides 91–509 of the sequence reported by Gerald et al. in U.S. Pat. No. 5,602,024 (nucleotides 56–474 of the sequence deposited by Gerald et al. in GenBank under accession number U56079) flanked by BamHI (5') and MunI (3') restriction enzyme sites. To construct a full length human NPY Y$_5$ receptor cDNA beginning at the second initiation codon, the plasmid pCR3.1-hY$_5$A was digested with BamHI and MunI restriction enzymes and the 5983 bp fragment containing the plasmid backbone and the 3' 983 bp of the human NPY Y$_5$ receptor cDNA was purified. This 5983 bp fragment was ligated to the 419 bp PCR product, which had also been digested with BamHI and MunI. This plasmid construct is known as pCR3.1-hY$_{5B}$. Subsequently, pCR3.1-hY$_5$B and the plasmid pcDNA3 (InVitrogen) were digested with the restriction enzymes BamHI and XbaI. The 1350 bp human NPY Y$_5$ cDNA and the pcDNA3 plasmid were purified and were ligated to one another. The resulting plasmid was designated pcDNA3-hY$_{5B}$. When transfected into COS1 cells, this construct did not yield detectable expression of the human Y$_5$ receptor. (Table 1) In a further effort to improve expression of the human NPY Y$_5$ receptor, the native 5' untranslated region of the human NPY Y$_5$ receptor was appended to the 5' end of pCR3.1-hY$_{5B}$. The native 5' untranslated region of the human NPY Y$_5$ receptor cDNA was isolated by 5' rapid amplification of cDNA ends (5' RACE) via the Elongase Kit from Life Technologies (Gaithersburg, Md.). PCR reactions were carried out in a 50 ul volume containing 100 ng DNA from a SK-N-MC cell cDNA library constructed in pcDNA3; 300 nM T7 (sense) primer (TAATACGACTCACTATAGGG (SEQ ID NO: 8)); 100 nM antisense primer (AAGGCATAATATGGCACATGAC (SEQ ID NO: 9) corresponding to nucleotides 424–445 of the sequence reported by Gerald et al. in U.S. Pat. No. 5,602,024 and nucleotides 389–410 of the sequence deposited by Gerald et al. in GenBank under accession number U56079); 200 uM each of dATP, dCTP, dGTP and dTTP; 60 mM Tris-SO$_4$ (pH 9.1); 18 mM (NH$_4$)$_2$SO$_4$; 1 ul Elongase enzyme mix; and 2 mM MgSO$_4$. The PCR reaction was initially denatured at 94° C. for 30 seconds. The PCR was then carried out for 35 cycles with each cycle of PCR consisting of denaturation at 94° C. for 30 seconds, annealing at 55° C. for 30 seconds, and elongation at 72° C. for 60 seconds. Subsequently, a final cycle of elongation was performed at 72° C. for 7 minutes. 5 ul of this PCR reaction was then reamplified under the same conditions except that the primers used were 300 nM T7 (sense) primer (TAATACGACTCACTATAGGG (SEQ ID NO: 10)) and 100 nM antisense primer (ACTTACAAATGTATAGAGCCC (SEQ ID NO: 11), corresponding to nucleotides 226–246 of the sequence reported by Gerald et al. in U.S. Pat. No. 5,602,024 and nucleotides 191–211 of the sequence deposited by Gerald et al. in GenBank under accession number U56079). The resulting 400 bp product was purified and ligated into pCR2.1 (InVitrogen) to yield the plasmid pCR2.1-hY$_5$ 5' UTR. Sequencing of pCR2.1-hY$_5$ 5' UTR revealed that the second initiation codon in the sequence reported by Gerald et al in U.S. Pat. No. 5,602,024 is actually the correct initiation codon. The sequence of the 5' end of the human NPY Y$_5$ cDNA diverged from the sequence reported by Gerald et al. at nucleotide 82 (nucleotide 47 of the sequence deposited by Gerald et al. in GenBank under accession number U56079). Subsequent analysis revealed that the sequence reported by Gerald et al. prior to the point of divergence from our sequence is actually genomic sequence rather than cDNA sequence. To construct a human NPY Y$_5$ receptor cDNA expression plasmid that incorporates the native 5' untranslated region of the cDNA, pcDNA3-hY$_{5B}$ was digested with BamHI, purified, ligated to EcoRI conversion linkers (New England Biolabs) and digested with EcoRI. Simultaneously, pCR2.1-hY$_5$ 5' UTR was digested with EcoRI and the 300 bp fragment corresponding to the 5' untranslated region of the human NPY Y$_5$ receptor DNA and the first 73 bp of the coding sequence was purified. The first 73 bp of the coding sequence correspond to nucleotides 91–164 of the sequence reported by Gerald et al. in U.S. Pat. No. 5,602,024 and nucleotides 56–129 of the sequence deposited by Gerald et al. in GenBank under accession number U56079. This 300 bp fragment was ligated to EcoRI digested pcDNA3-hY$_{5B}$. The resulting plasmid, designated pcDNA3-hY$_{5D}$, contains a 1633 bp DNA insert (SEQ ID NO: 20) consisting of a 6 bp BamH1 site, 254 bp of 5' untranslated sequence, the entire 1338 bp coding region, 29 bp of the 3' untranslated region of the human NPY Y$_5$ receptor cDNA and a 6 bp Xba1 site. Subsequently, pcDNA3-hY$_{5D}$ was digested with BamHI and Xbal and the 1621 bp hY$_{5D}$ cDNA construct was purified and ligated to the expression vector pcDNA3.1 that had been also been digested with BamHI and Xbal. The resulting construct was designated pcDNA3.1-hY$_{5D}$. When transfected into COS1 cells, this construct did yield reasonable levels of expression of the human Y$_5$ receptor. Therefore, the correct coding sequence and the presence of native 5' untranslated sequence is critical for expression of the native human Y$_5$ receptor.

Isolation of the Rat NPY Y$_5$ Receptor cDNA

Rat hypothalamus poly A$^+$ RNA was purchased from Clontech (Palo Alto, Calif.). Rat hypothalamus cDNA was prepared by reverse transcription with the GeneAmp RNA PCR Kit (Perkin Elmer, Norwalk, Conn.). Reverse transcription was performed in a 20 ul reaction mixture containing 200 ng of rat hypothalamus poly A$^+$ RNA; 10 mM Tris-Cl (pH 8.3); 5 mM MgCl$_2$; 50 mM KCl; 1 mM each of dATP, dCTP, dTTP and dGTP; 1U RNase inhibitor; 2.5 U murine Moloney leukemia virus reverse transcriptase; and 0.15 uM oligonucleotide primer having the sequence GGGCTCGAGGCACAGAGAGAATCATGACATGTG (SEQ ID NO: 12). Nucleotides 10–33 of this primer correspond to nucleotides 1420–1443 of the sequence reported by Gerald et al. in U.S. Pat. No. 5,602,024 and to nucleotides 1385–1408 of the sequence deposited by Gerald et al. in GenBank under accession number U56078. The reverse transcription mixture was placed in a Perkin Elmer 9600 thermocycler and subjected to one cycle of 42° C. for 15 minutes, 99° C. for 5 minutes and 5° C. for 5 minutes.

The rat NPY Y$_5$ receptor cDNA was isolated via the PCR. The PCR reaction consisted of 10 mM Tris Cl (pH 8.3), 2 mM MgCl$_2$, 50 mM KCl, 2 ul of rat hypothalamus cDNA from the reverse transcription reaction and 15 pmol of the oligonucleotide primers GGGGGATCCGCTGCTAATGGACGTCCTCTTCTT (SEQ ID NO: 13) (sense primer) and GGGCTCGAGGCACAGAGAGAATCATGACATGTG (SEQ ID NO: 14) (antisense primer). Nucleotides 10–33 of the sense primer correspond to nucleotides 54–77 of the sequence reported by Gerald et al. in U.S. Pat. No. 5,602,024 and to nucleotides 19–42 of the sequence deposited by Gerald et al. in GenBank under accession number U56078. Nucleotides 10–33 of the antisense primer correspond to nucleotides 1420–1443 of the sequence reported by Gerald et al. in U.S. Pat. No. 5,602,024 and to nucleotides 1385–1408 of the sequence deposited by Gerald et al. in GenBank under accession number U56078. The PCR reaction was initially denatured at 94° C. for 1 minute. The PCR was then carried out for 35 cycles with each cycle of PCR consisting of denaturation at 94° C. for 30 seconds, annealing at 57° C. for 30 seconds, and elongation at 72° C. for 30 seconds. Subsequently, a final cycle of elongation was performed at 72° C. for 7 minutes. The reaction was then held at 4° C. until use. A 1402 bp product flanked by 5' BamHI and 3' Xhol restriction enzyme sites was obtained in this PCR reaction and was confirmed by DNA sequence analysis to incorporate nucleotides 54–1443 of the sequence reported by Gerald et al in U.S. Pat. No. 5,602,024 and nucleotides 19–1408 of the sequence deposited by Gerald et al. in GenBank under accession number U56078. This 1402 bp product was ligated into the plasmid pCR3.1 (InVitrogen) to yield a construct known as pCR3.1-rY$_{5A}$. When transfected into COS1 cells, this construct yielded reasonable expression of the rat Y$_5$ receptor (Table 1).

As was the case with the human NPY Y$_5$ receptor cDNA, examination of the sequence of the 1402 bp rat NPY Y$_5$ receptor cDNA and the sequences reported by Gerald et al. in U.S. Pat. No. 5,602,024 and GenBank accession number U56078 revealed that there were two in frame initiation codons at the 5' end of the cDNA. In an effort to improve expression of the rat NPY Y$_5$ receptor, the 1402 bp rat NPY Y$_5$ receptor cDNA was modified to remove the first initiation codon and the intervening nucleotides between the first and second initiation codons. In addition, a Kozak consensus sequence was added to improve expression. This was accomplished by the PCR. The PCR reaction consisted of 20 mM Tris-Cl (pH 8.8); 2 mM MgSO$_4$; 10 mM KCl; 10 mM (NH$_4$)$_2$SO$_4$; 0.1% Triton X-100; 100 ug/ml bovine serum albumin; 25 mM each of dATP, dTTP, dCTP and dGTP; 5 U Pfu polymerase (Stratagene, La Jolla, Calif.); 100 ng pCR3.1-rY$_{5A}$; and 15 pmol of the oligonucleotide primers TTTGGATCCACCATGGAGTTTAAG (SEQ ID NO:15) (sense primer) and AGGAAGTAGCCATGGTTTGCCGTT (SEQ ID NO: 16) (antisense primer). Nucleotides 13–24 of the sense primer correspond to nucleotides 94–105 of the sequence reported by Gerald et al. in U.S. Pat. No. 5,602,024 and to nucleotides 59–70 of the sequence deposited by Gerald et al. in GenBank under accession number U56078. The antisense primer corresponds to nucleotides 546–569 of the sequence reported by Gerald et al. in U.S. Pat. No. 5,602,024 and to nucleotides 511–534 of the sequence deposited by Gerald et al. in GenBank under accession number U56078. The PCR reaction was initially denatured at 94° C. for 1 minute. The PCR was then carried out for 35 cycles with each cycle of PCR consisting of denaturation at 94° C. for 45 seconds, annealing at 55.2° C. for 45 seconds, and elongation at 72° C. for 1 minute. The reaction was then held at 4° C. until use. This PCR reaction yielded a 420 bp product that incorporated nucleotides 94–569 of the sequence reported by Gerald et al. in U.S. Pat. No. 5,602,024 and nucleotides 59–534 of the sequence deposited by Gerald et al. in GenBank under accession number U56078 flanked by BamHI (5') and Munl (3') restriction enzyme sites. To construct a full length rat NPY Y$_5$ receptor cDNA beginning at the second initiation codon, the plasmid pCR3.1-rY$_{5A}$ was digested with BamHI and Munl restriction enzymes and the 5982 bp fragment containing the plasmid backbone and the 3' 982 bp of the rat NPY Y$_5$ receptor cDNA was purified. This 5982 bp fragment was ligated to the 420 bp PCR product, which had also been digested with BamHI and Munl. This plasmid construct is known as pCR3.1-rY$_{5B}$. This construct yielded low but detectable levels of the rat Y$_5$ receptor when transfected into COS1 cells.

In a further effort to improve expression of the rat NPY Y$_5$ receptor, the native 5' untranslated region of the rat NPY Y$_5$ receptor was appended to the 5' end of pCR3.1-rY$_{5B}$. The native rat NPY Y$_5$ 5' untranslated sequence was isolated by the PCR. Rat brain poly A$^+$ RNA was purchased from Clontech. Rat brain cDNA was prepared by reverse transcription with the Perkin Elmer GeneAmp RNA PCR kit. The reverse transcription reaction was performed in a 20 ul volume containing 200 ng rat brain poly A$^+$ RNA; 10 mM Tris-Cl (pH 8.3); 5 mM MgCl$_2$; 50 mM KCl; 1 mM each of dATP, dTTP, dCTP and dGTP; 1 U RNase inhibitor; 2.5 U murine Moloney leukemia virus reverse transcriptase; and 0.15 uM oligonucleotide primer having the sequence GGAGCAAAACAGGACGAC (SEQ ID NO: 17). This primer corresponds to nucleotides 509–526 of the sequence deposited in GenBank by Hu et al. under accession number U66274. The reverse transcription mixture was placed in a Perkin Elmer 9600 thermocycler and subjected to one cycle of 42° C. for 15 minutes, 99° C. for 5 minutes and 5° C. for 5 minutes. The entire reverse transcription reaction containing rat brain cDNA was then used in a PCR reaction that also included 10 mM Tris-Cl (pH 8.3); 3 mM $MgCl_2$; 50 mM KCl; 0.15 uM oligonucleotide primers CGCGGATC-CCCGAGGTGCTTCTAAAAC (SEQ ID NO: 18) (sense primer) and GGAGCAAAACAGGACGAC (SEQ ID NO: 19) (antisense primer). Nucleotides 10–27 of the sense primer correspond to nucleotides 72–89, while the antisense primer corresponds to nucleotides 509–526 of the sequence deposited in GenBank by Hu et al. under accession number U66274. The PCR reaction was initially denatured at 94° C. for 105 seconds. The PCR was then carried out for 35 cycles with each cycle of PCR consisting of denaturation at 94° C. for 60 seconds, annealing at 54° C. for 60 seconds, and elongation at 72° C. for 60 seconds. Subsequently, a final cycle of elongation was performed at 72° C. for 7 minutes. The reaction was then held at 4° C. until use. Two products of 446 bp and 569 bp were obtained in this PCR reaction and were ligated into the pCR3.1 vector (InVitrogen). Sequencing revealed that the 446 bp product was identical to nucleotides 72–509 of the sequence deposited by Hu et al. in GenBank under accession number U66274 with the exception of nucleotide 237 (C in our sequence vs. T in the sequence of Hu et al.). The 569 bp product was also identical to the sequence deposited in GenBank under accession number U66274 except that it had a 123 bp insertion between nucleotides 232 and 233 of GenBank sequence U66274. This product also had the same single nucleotide transversion as the first product (i.e. nucleotide 237 of GenBank sequence U66274 converted from T to C in our sequence). This second product in pCR3.1 was designated pCR3.1-$rY_5$ 5' UTR. To construct a rat NPY $Y_5$ receptor cDNA expression plasmid that incorporates the native 5' untranslated region of the cDNA, the plasmid pCR3.1-$rY_{5A}$ was digested with the Kpnl and Xbal and the rat NPY $Y_5$ receptor cDNA was purified and ligated into pUC18 that had also been digested with Kpnl and Xbal. The resulting plasmid was designated pUC18-$rY_{5A}$. pUC18-$rY_{5A}$ was then digested with BamHI and BseRI and the resulting 3966 bp fragment was purified. This fragment consists of 2659 bp of pUC18 backbone and the 3' 1307 bp of the rat NPY $Y_5$ cDNA. Simultaneously, pCR3.1-$rY_5$ 5' UTR was digested with BamHI and BseRI and the resulting 322 bp fragment consisting of nucleotides 72–272 of GenBank sequence U66274 as well as the novel 123 bp insertion between nucleotides 232 and 233 was purified. These two fragments were ligated to give the construct designated pUC18-$rY_{5C}$. Finally, pUC18-$rY_{5C}$ was digested with BamHI and Xbal and the resulting 1655 $rY_{5C}$ cDNA (SEQ ID NO: 22) was purified and ligated into pcDNA3.1 that had also been digested with BamHI and Xbal. This construct was designated pcDNA3.1-$rY_{5C}$. When transfected into COS1 cells, this construct yielded reasonable expression of the rat $Y_5$ receptor (Table 1).

Preparation of the Rat/Human Chimeric NPY $Y_5$ Receptor cDNA

The expression of the pcDNA3-$rY_{5C}$ construct was significantly better than the similar pcDNA3.1-$hY_{5D}$ construct (see data in Table 1). The major differences between these two constructs are in the sequence of the 5' untranslated region and in the sequence of the extreme 5' end of the coding region. Therefore, a chimeric construct was constructed in which the 5' untranslated region and the extreme 5' end of the coding region of the rat NPY $Y_5$ receptor cDNA from the pcDNA3-$rY_{5C}$ construct was substituted for the corresponding region of the pcDNA3.1-$hY_{5D}$ construct. pcDNA3.1-$hY_{5D}$ was digested with Munl and the resulting 5.62 kb fragment was purified. This fragment contains a 4.65 kb piece of the pcDNA3.1 vector (nucleotides 983–161) and nucleotides 661–1633 of the $hY_{5D}$ cDNA sequence. Simultaneously, pcDNA3-$rY_{5C}$ was also digested with Munl and the resulting 1.47 kb fragment was purified. This fragment contains nucleotides 161–930 of the pcDNA3 vector and nucleotides 1–700 of the $rY_{5C}$ cDNA sequence. The 5.62 kb Munl fragment from pcDNA3.1-$hY_{5D}$ and the 1.47 kb Munl fragment from pcDNA3-$rY_{5C}$ were ligated to generate a construct in the pcDNA3.1 vector backbone that consisted of the first 700 bp of the $rY_{5C}$ cDNA sequence appended to nucleotides 661–1633 of the $hY_{5D}$ cDNA sequence. Subsequently, nucleotides 495 and 634 of the $Y_5$ sequence were changed from G to C and C to T, respectively, with the QuikChange Site-Directed Mutagenesis kit (Stratagene). This resulted in the conversion of $Val^{66}$ and $Ala^{112}$ encoded by the $rY_{5C}$ cDNA to the corresponding amino acids encoded by the $hY_{5D}$ cDNA (Leu and Val, respectively). The resulting plasmid was designated pcDNA3.1-$rhY_5$ and contains a 1672 bp DNA insert (SEQ ID NO: 1) consisting of the 5' untranslated region (299 bp) as well as the first 105 bp of the coding sequence of the $rY_{5C}$ construct appended to nucleotides 365–1633 of the $hY_{5D}$ cDNA sequence. The protein encoded by this construct consists of the first 35 amino acids of the rat $Y_5$ receptor appended to amino acids 36–445 of the human $Y_5$ receptor. When transfected into COS1 cells, this construct yielded levels of expression higher than the native human $Y_5$ receptor and similar or greater levels of expression than the native rat $Y_5$ receptor. The pharmacological properties of this hybrid receptor were similar to those of the native human $Y_5$ receptor (Table 2).

Transfection of COS1 Cells

COS1 cells were obtained from the American Type Culture Collection (Rockville, Md.). COS1 cells were maintained in Dulbecco's modified Eagle's medium (DMEM) supplemented with 10% heat inactivated fetal calf serum and were grown at 37° C., 5% $CO_2$. The cells were seeded at $3 \times 10^6$ cells/150 mm tissue culture dish in DMEM supplemented with 10% heat inactivated fetal calf serum. Twenty four hours later, the medium was replaced with DMEM supplemented with 10% heat inactivated fetal calf serum, 20 mM HEPES (pH 7.3), 100 U/ml penicillin, 100 ug/ml streptomycin, 1 ug/ml NPY $Y_5$ receptor expression plasmid, 50 ug/ml DEAE dextran, 100 uM chloroquine and the cells were incubated in this solution for 3.5 hours. The cells were subsequently incubated for 2–3 minutes with 10% dimethyl sulfoxide in Dulbecco's phosphate buffered saline (PBS), washed once with PBS and incubated 60–72 hours in DMEM supplemented with 10% fetal calf serum, 100 U/ml penicillin and 100 ug/ml streptomycin.

Transfection of CHO Cells

CHO cells were plated at $1 \times 10^6$ cells/dish in 100 mm dishes in Ham's F12 medium (Life Technologies) supplemented with 10% heat inactivated fetal calf serum (ICN, Costa Mesa, Calif.). Twenty four hours later, 8 ug of pcDNA3.1-$rhY_5$ was transfected into the CHO cells with lipofectamine (Life Technologies) according to the manufacturer's instructions. After incubating the cells for 24 hours with the lipofectamine/pcDNA3.1-$rhY_5$ mixture, the medium was aspirated and replaced with fresh Ham's F12 medium/10% heat inactivated fetal calf serum. Twenty four hours later (48 hours after initiation of transfection), the cells were detached from the dish with trypsin/EDTA (Life Technologies) and replated at approximately $1 \times 10^8$ to $1 \times 10^9$ cells/dish in new 100 mm dishes in Ham's F12 medium supplemented with 10% heat inactivated fetal calf serum and 400 ug/ml G418 (Life Technologies). The medium was replaced every 3–4 days with fresh Ham's F12 medium supplemented with 10% heat inactivated fetal calf serum and 400 ug/ml G418. When single, well-isolated colonies were evident (usually after 1–2 weeks), cloning cylinders were placed around individual colonies and the cells in each colony were removed from the dish with trypsin/EDTA. Cells from individual colonies were transferred to 24 well plates and expanded to generate individual cell lines. The cell lines were then screened for binding of [$^{125}$I]PYY as described below to identify cell lines expressing the rhY$_5$ receptor. Cell lines expressing the rhY$_5$ receptor were maintained in Ham's F12 medium supplemented with 10% heat-inactivated fetal calf serum and 200 ug/ml G418.

Preparation of COS1 and CHO Cell Membranes

COS1 or CHO cells were placed on ice and washed once with ice cold PBS. The cells are scraped into membrane buffer (50 mM HEPES [pH 7.2], 0.25 mg/ml Pefabloc [Boehringer Mannheim, Indianapolis, Ind.], 25 ug/ml leupeptin [Sigma, St. Louis, Mo.], 25 ug/ml aprotinin [Sigma]), transferred to a Dounce homogenizer and homogenized on ice. The homogenate is centrifuged at 15,000 rpm in a Sorvall SS34 rotor at 4° C. and the membrane pellet is resuspended in membrane buffer via homogenization. The homogenate is again centrifuged at 15,000 rpm in a Sorvall SS34 rotor at 4° C. and the membrane pellet is resuspended in membrane buffer via homogenization. The membrane homogenate is then stored frozen at −80° C. until use.

Radioligand Binding to NPY Receptors

Binding of [$^{125}$I] porcine peptide YY (PYY) (NEN, Boston, Mass., 2200 Ci/mmol) to the NPY receptors expressed in COS or CHO cell membranes was performed in binding buffer (50 mM HEPES [pH 7.2], 0.1% bovine serum albumin [RIA grade], 2.5 mM CaCl$_2$, and 1 mM MgCl$_2$). Saturation binding assays were performed in binding buffer containing 0.01–2 nM [$^{125}$I] PYY and 2.5–5 ug of membrane protein (50 ul final volume). Competition binding assays were carried out in binding buffer containing 5–10 ug membrane protein, 0.1 nM [$^{125}$I] PYY and various concentrations of competing peptides (200 ul final volume). In all cases, nonspecific binding was defined as binding in the presence of 1 uM unlabeled human NPY. to determine nonspecific binding. Binding assays were incubated at room temperature for 90 minutes and were terminated by rapid vacuum filtration through glass fiber filters in 96-well format (Multiscreen FB Filter Plates, Millipore, Bedford, Mass. or Unifilter-96 GF/C, Packard, Meriden, Conn.) Prior to filtration the glass fiber filters were pretreated with 100 ul of 0.3 % polyethylenimine. Each filter was then washed 3 times with 100 ul of PBS. Radioactivity trapped on the filters was then counted by standard gamma counting techniques.

Assay of Inhibition of Forskolin-Stimulated cAMP Formation by NPY Receptors

CHO cells expressing NPY receptors were seeded into 96-well, flat-bottom tissue culture plates at a density of 20,000 cells per well. After approximately 48 hours, the cell monolayers were rinsed twice with Hank's balanced salt solution (HBSS; Life Technologies), then preincubated for 10 minutes at 37° C. with 125 μl/well of assay buffer (HBSS supplemented with 4 mM MgCl$_2$, 10 mM HEPES, 0.2% BSA, 1 mM 3-isobutyl-1-methylxanthine [IBMX, Sigma Chemical Co., St. Louis, Mo.]). Subsequently, the assay buffer was removed and replaced with assay buffer containing 1 μM forskolin (Sigma) and various concentrations of NPY or NPY analogues. After 10 minutes at 37° C., the medium was removed and 75 μl of ethanol was added to the cell monolayers. The tissue culture plates were agitated on a platform shaker for 15 minutes after which the plates were transferred to a warm water bath to evaporate the ethanol. The cell residues were dissolved in 200–250 μl FlashPlate assay buffer. The amount of cAMP in each well was quantified using the [$^{125}$I]-cAMP FlashPlate kit (Dupont-NEN, Boston, Mass.) according to the manufacturer's protocol.

Radioligand Binding Data

The level of expression of the various NPY Y$_5$ receptor constructs after transient expression in COS1 cells is shown in Table 1.

TABLE 1

The level of expression of each receptor construct was measured by radioligand binding at an [$^{125}$I]pYY concentration of 100 pM. All receptors were expressed transiently in COS1 cells.

| Receptor Construct | Level of Expression (fmol/mg protein) |
| --- | --- |
| pCR3.1-hY$_{5A}$ | 0 |
| pcDNA3-hY$_{5B}$ | 0 |
| pcDNA3.1-hY$_{5D}$ | 103 |
| pcDNA3.1-rhY$_5$ | 298 |
| pCR3.1-rY$_{5A}$ | 100 |
| pCR3.1-rY$_{5B}$ | 38 |
| pcDNA3.1-rY$_{5C}$ | 225 |

The affinity of a series of peptides for the rhY$_5$ receptor construct was very similar to that of the native human Y$_5$ receptor construct as shown in Table 2.

TABLE 2

Affinity of NPY and related peptides for the human Y$_5$ receptor and the rat/human hybrid Y$_5$ receptor. Peptide affinities were measured in competition binding assays with membranes from COS1 cells transiently expressing the human Y$_5$ and rat/human hybrid Y$_5$ receptors.

| | K$_i$ (nM) | |
| --- | --- | --- |
| Peptide | Human Y$_5$ | Hybrid Y$_5$ |
| NPY | 1.36 | 0.64 |
| NPY (13–36) | 11.5 | 12.6 |
| [Leu$^{31}$, Pro$^{34}$]NPY | 5.1 | 0.76 |
| Human PP | 1.6 | 2.86 |
| Rat PP | 60 | 75.6 |

Assay for Identification of an NPY Y$_5$ Receptor Antagonist

Because the rhY$_5$ receptor cDNA can be expressed at high levels in mammalian cells, it can be used to screen for ligands that bind to the human Y$_5$ receptor. In a typical assay, membranes from mammalian cells expressing the rhY$_5$ receptor are incubated with [$^{125}$I]PYY and either vehicle (typically dimethyl sulfoxide) or test substances dissolved in vehicle. All assays are incubated in round bottom 96 well plates or, alternatively, in higher density plate formats. The assay is carried out as described in the preceding section (Radioligand Binding to NPY Receptors). The test substances are initially tested at a single concentration of between 10$^{-6}$ to 10$^{-5}$ M. Test substances can either be screened individually or as mixtures of test substances (typically 8–10 test substances per assay). Test substances that inhibit [$^{125}$I]PYY binding to a level greater than or equal to 50% of the [$^{125}$I]PYY binding observed in the presence of the vehicle alone are considered to be active. Active test substances are then tested over a range of concentrations (typically $10^{-12}$ to $10^{-5}$M) and the equilibrium dissociation constant of the test substance at the rhY$_5$ receptor is determined. The equilibrium dissociation constant of the test substance can be determined by calculating the amount of [$^{125}$I]PYY binding at each concentration of the test substance and plotting these values as a function of the concentration of test substance. These data can then be fit to a logistic function by standard curve fitting software. Such software can then calculate the concentration of test substance that reduces [$^{125}$I]PYY binding to 50% of the level of [$^{125}$I]PYY binding observed in the presence of vehicle alone. This concentration of test substance is referred to as the IC$_{50}$. The equilibrium dissociation constant can then be determined according to the following equation described by Cheng and Prusoff (11):

$$K_i = IC_{50}/(1+([L]/K_D))$$

where $K_i$ is the equilibrium dissociation constant of the test substance for the Y$_5$ receptor, IC$_{50}$ is the concentration of test substance that reduces [$^{125}$I]PYY binding to 50% of the level of [$^{125}$I]PYY binding observed in the presence of vehicle alone, [L] is the concentration of [$^{125}$I]PYY used in the assay and $K_D$ is the equilibrium dissociation constant of [$^{125}$I]PYY for the NPY Y$_5$ receptor. Test substances having equilibrium dissociation constants of 10 nM or less would be considered to be potential drug candidates.

An alternative assay would be to use scintillation proximity assay (SPA) technology to perform the radioligand binding assay. In this assay, mammalian cell membranes expressing the rhY$_5$ receptor are incubated with SPA beads (Amersham, Naperville, Ill.), [$^{125}$I]PYY and test substances. During the reaction, membranes bind to the SPA beads and [$^{125}$I]PYY and test substances compete for binding to the Y$_5$ receptor. After a sufficient time, the reactions are placed in a scintillation counter and the amount of [$^{125}$I]PYY bound to the rhY$_5$ receptor is quantitated by scintillation counting.

An alternative assay would be to determine the effect of test substances on the inhibition of forskolin-stimulated cAMP formation mediated by the Y$_5$ receptor. To identify compounds that activate the rhY$_5$ receptor (i.e. Y$_5$ receptor agonists), test substances would be substituted for NPY in the standard assay described above. The test substances are initially tested at a single concentration of between $10^{-6}$ to $10^{-5}$ M. Test substances can either be screened individually or as mixtures of test substances (typically 8–10 test substances per assay). Test substances that give greater than 20% inhibition of forskolin-stimulated cAMP formation would be considered to be active. Active test substances are then tested over a range of concentrations (typically $10^{-12}$ to $10^{-5}$M) and the EC$_{50}$ would be determined. The EC$_{50}$ is defined as the concentration of test substance that gives 50% of the maximal inhibition of forskolin-induced cAMP formation attainable. Compounds having an EC$_{50}$ less than 10 nM would be considered to be potential drug candidates. To identify compounds that are antagonists of the rhY$_5$ receptor, test substances would be screened for their ability to inhibit the NPY-induced decrease in forskolin-stimulated cAMP formation. NPY is usually used at a concentration of $10^{\times 8}$ to $10^{-7}$ M while the test substances are initially tested at a single concentration of $10^{-6}$ to $10^{-5}$ M. Test substances can either be screened individually or as mixtures of test substances (typically 8–10 test substances per assay). Test substances that give greater than 50% inhibition of the NPY-induced decrease in forskolin-stimulated cAMP formation are considered to be active. Active test substances are then tested over a range of concentrations (typically $10^{-12}$ to $10^{-5}$M) and the IC$_{50}$ would be determined. The IC$_{50}$ is defined as the concentration of test substance that gives a 50% inhibition of the NPY-induced decrease of forskolin-induced cAMP formation. Compounds having an EC$_{50}$ less than 10 nM would be considered to be potential drug candidates.

Literature Cited

1. Wahlestedt, C. and Reis, D. J.: Neuropeptide Y-related peptides and their receptors-Are the receptor potential therapeutic drug targets? Annu. Rev. Pharmacol. Toxicol. 32: 309–352, 1993.
2. Blomqvist, A. G. and Herzog, H.: Y-receptor subtypes—how many more? Trends Neurosci 20: 294–298, 1997.
3. Gerald, C., Walker, M. W., Criscione, L., Gustafson, E. L., Batzl-Hartmann, C., Smith, K. E., Vaysse, P., Durkin, M. M., Laz, T. M., Linemeyer, D. L., Schaffhauser, A. O., Whitebread, S., Hofbauer, K. G., Taber, R. I., Branchek, T. A. and Weinshank, R. L.: A receptor subtype involved in neuropeptide-Y-induced food intake (see comments). Nature 382: 168–171, 1996.
4. Woldbye, D. P., Larsen, P. J., Mikkelsen, J. D., Klemp, K., Madsen, T. M. and Bolwig, T. G.: Powerful inhibition of kainic acid seizures by neuropeptide Y via Y5-like receptors (see comments). Nat Med 3: 761–764, 1997.
5. Bischoff, A., Avramidis, P., Erdbrugger, W., Munter, K. and Michel, M. C.: Receptor subtypes Y1 and Y5 are involved in the renal effects of neuropeptide Y. Br J Pharmacol 120: 1335–1343, 1997.
6. Akabayashi, A., Watanabe, Y., Wahlestedt, C., McEwen, B. S., Paez X. and Leibowitz, S. F.: Hypothalamic neuropeptide Y, its gene expression and receptor activity: relation to circulating corticosterone in adrenalectomized rats. Brain Res 665: 201–212, 1994.
7. Dube, M. B., Xu, B., Crowley, W. R., Kalra, P. S. and Kalra, S. P.: Evidence that neuropeptide Y is a physiological signal for normal food intake. Brain Res 646: 341–344, 1994.
8. Wilding, J. P., Gilbey, S. G., Bailey, C. J., Batt, R. A., Williams, G., Ghatei, M. A. and Bloom, S. R.: Increased neuropeptide-Y messenger ribonucleic acid (mRNA) and decreased neurotensin mRNA in the hypothalamus of the obese (ob/ob) mouse. Endocrinology 132: 1939–1944, 1993.
9. Erickson, J. C., Hollopeter, G. and Palmiter, R. D.: Attenuation of the obesity syndrome of ob/ob mice by the loss of neuropeptide Y. Science 274: 1704–1707, 1996.
10. Stephens, T. W., Basinski, M., Bristow, P. K., Bue-Valleskey, J. M., Burgett, S. G., Craft, L., Hale, J., Hoffmann, J., Hsiung, H. M., Kriaciunas, A. et al.: The role of neuropeptide Y in the antiobesity action of the obese gene product. Nature 377: 530–532, 1995.
11 Cheng, Y. and Prusoff, W. H.: Relationship between the inhibition constant ($K_i$) and the concentration of inhibitor which causes 50 percent inhibition ($I_{50}$) of an enzymatic reaction. Biochem. Pharmacol. 22:3099–3108, 1973.

What is claimed is:

1. A chimeric polypeptide comprising an amino acid sequence defined by SEQ ID NO: 2.

2. A nucleic acid encoding a chimeric polypeptide comprising the amino acid sequence as set forth in SEQ ID NO: 2.

3. An expression vector comprising the nucleic acid of claim 2 operably linked to a genetic control element that regulates expression of the nucleic acid in a host cell.

4. A host cell comprising the expression vector of claim 3.

5. A method for making a chimeric polypeptide comprising culturing a host cell of claim 4 under conditions in which the nucleic acid is expressed and isolating the polypeptide from culture.

* * * * *